United States Patent
Krishnan

(10) Patent No.: US 7,981,946 B2
(45) Date of Patent: *Jul. 19, 2011

(54) ANTIMICROBIAL AND ANTISTATIC POLYMERS AND METHODS OF USING SUCH POLYMERS ON VARIOUS SUBSTRATES

(75) Inventor: Venkataram Krishnan, Cary, NC (US)

(73) Assignee: Mallard Creek Polymers, Inc., Charlotte, NC (US)

( * ) Notice: Subject to any disclaimer, the term of this patent is extended or adjusted under 35 U.S.C. 154(b) by 443 days.

This patent is subject to a terminal disclaimer.

(21) Appl. No.: 12/116,021

(22) Filed: May 6, 2008

(65) Prior Publication Data

US 2008/0226584 A1    Sep. 18, 2008

Related U.S. Application Data

(63) Continuation-in-part of application No. 10/882,570, filed on Jul. 1, 2004, now Pat. No. 7,491,753.

(60) Provisional application No. 60/484,745, filed on Jul. 3, 2003.

(51) Int. Cl.
C09D 5/16 (2006.01)
(52) U.S. Cl. ......... 523/122; 424/405; 428/364; 524/804
(58) Field of Classification Search .................. 424/405; 428/364; 523/122; 524/804
See application file for complete search history.

(56) References Cited

U.S. PATENT DOCUMENTS

| | | | |
|---|---|---|---|
| 2,882,157 A | 4/1959 | Thompson et al. |
| 2,972,535 A | 2/1961 | Laasko et al. |
| 3,140,227 A | 7/1964 | Roth et al. |
| 3,227,672 A | 1/1966 | Fertig et al. |
| 3,262,807 A | 7/1966 | Sterman et al. |
| 3,296,167 A | 1/1967 | Turner et al. |
| 3,296,196 A | 1/1967 | Lamoreaux |
| 3,450,794 A | 6/1969 | Ebneth et al. |
| 3,592,805 A | 7/1971 | Szabo et al. |
| 3,619,200 A | 11/1971 | Ferguson et al. |
| 3,753,716 A | 8/1973 | Ishihara et al. |
| 3,872,128 A | 3/1975 | Byck |
| 4,017,440 A | 4/1977 | Killam |
| 4,026,941 A | 5/1977 | Login et al. |
| 4,029,694 A | 6/1977 | Weipert et al. |
| 4,070,189 A | 1/1978 | Kelley et al. |
| 4,080,315 A | 3/1978 | Login |
| 4,081,419 A | 3/1978 | Shimizu et al. |
| 4,093,676 A | 6/1978 | Weipert et al. |
| 4,098,842 A | 7/1978 | Login |
| 4,104,443 A | 8/1978 | Latta et al. |
| 4,147,550 A | 4/1979 | Campbell et al. |
| 4,226,748 A | 10/1980 | Matsunaga et al. |
| 4,229,554 A | 10/1980 | Newkirk et al. |
| 4,234,381 A | 11/1980 | Killam |
| 4,256,800 A | 3/1981 | Stockhausen et al. |
| 4,332,919 A | 6/1982 | Kobayashi et al. |
| 4,361,623 A | 11/1982 | Newkirk et al. |
| 4,366,238 A | 12/1982 | Yokoyama et al. |
| 4,377,667 A | 3/1983 | Sakurai et al. |
| 4,384,078 A | 5/1983 | Ohya et al. |
| 4,416,668 A | 11/1983 | Thompson |
| 4,500,517 A | 2/1985 | Luss |
| 4,506,070 A | 3/1985 | Ben |
| 4,543,390 A | 9/1985 | Tanaka et al. |
| 4,546,140 A | 10/1985 | Shih |
| 4,617,343 A | 10/1986 | Walker et al. |
| 4,632,881 A | 12/1986 | Trotz et al. |
| 4,668,748 A | 5/1987 | Hardam et al. |
| 4,722,965 A | 2/1988 | Wong et al. |
| 4,735,991 A | 4/1988 | Guioth et al. |
| 4,740,546 A | 4/1988 | Masuda et al. |
| 4,810,567 A | 3/1989 | Calcaterra et al. |
| 4,831,098 A | 5/1989 | Watanabe et al. |
| 4,841,021 A | 6/1989 | Katritzky et al. |
| 4,857,585 A | 8/1989 | Leising |
| 4,857,590 A | 8/1989 | Gaggar et al. |
| 4,859,727 A | 8/1989 | Sasaki et al. |
| 4,877,687 A | 10/1989 | Azegami et al. |
| 4,891,306 A | 1/1990 | Yokoyama et al. |
| 4,898,908 A | 2/1990 | Lahalih et al. |
| 4,900,543 A | 2/1990 | Ritter et al. |

(Continued)

FOREIGN PATENT DOCUMENTS

DE    2447611    4/1975
(Continued)

OTHER PUBLICATIONS

Napper, "Steric Stabilization", *J. Colloid Interface Sci.*, 58:2, 390-407 (1977), Abstract: 86: 107053, XP002125110.
Ottewill et al., "Preparation of Core-Shell Polymer Colloid Particles by Encapsulation", *Colloid & Polymer Science*, pp. 274-283 (1997).
International Search Report, PCT/US99/17670, International Filing Date: Aug. 6, 1999.
"Polymer Compositions for Cationic Electrodepositable Coatings", *Journal of Coatings Technology*, vol. 54; No. 686, Mar. 1982.
Rompp Chemie Lexikon (Chemical Dictionary), vol. 5, PI-S (1995), pp. 3558-3559.

(Continued)

*Primary Examiner* — Edward J Cain
(74) *Attorney, Agent, or Firm* — Womble Carlyle Sandridge & Rice, PLLC; Mark D. Jenkins

(57) ABSTRACT

The present invention relates to a substrate having one or more antimicrobial or antistatic properties. Such properties are imparted by applying a coating or film formed from a cationically-charged polymer composition. The polymer composition includes a noncationic ethylenically unsaturated monomer and an ethylenically unsaturated monomer capable of providing a cationic charge to the polymer composition. Optionally, the polymer composition includes a steric stabilization component incorporated into the cationically-charged polymer composition. The present invention also relates to a personal care product and polymeric material comprising a base polymer blended with the above cationically-charged polymer composition.

136 Claims, No Drawings

U.S. PATENT DOCUMENTS

| | | | |
|---|---|---|---|
| 4,900,544 A | 2/1990 | Ritter et al. |
| 4,920,166 A | 4/1990 | Buysch et al. |
| 4,931,506 A | 6/1990 | Yu |
| 4,943,612 A | 7/1990 | Morita et al. |
| 4,948,720 A | 8/1990 | Chen et al. |
| 4,954,636 A | 9/1990 | Merianos et al. |
| 4,981,936 A | 1/1991 | Good et al. |
| 4,997,697 A | 3/1991 | Malhotra |
| 4,999,249 A | 3/1991 | Deschler et al. |
| 5,010,139 A | 4/1991 | Yu |
| 5,024,840 A | 6/1991 | Blakely et al. |
| 5,043,195 A | 8/1991 | Skrivseth |
| 5,059,629 A | 10/1991 | Patton et al. |
| 5,061,752 A | 10/1991 | Buysch et al. |
| 5,081,182 A | 1/1992 | Robinson et al. |
| 5,142,010 A | 8/1992 | Olstein |
| 5,153,321 A | 10/1992 | Finter et al. |
| 5,175,059 A | 12/1992 | Yamamoto et al. |
| 5,194,539 A | 3/1993 | Charmot et al. |
| 5,247,008 A | 9/1993 | Michels et al. |
| 5,290,894 A | 3/1994 | Melrose et al. |
| 5,312,863 A | 5/1994 | Van Rheenen et al. |
| 5,314,924 A | 5/1994 | Lee |
| 5,346,956 A | 9/1994 | Gnanou |
| 5,358,688 A | 10/1994 | Robertson |
| 5,369,179 A | 11/1994 | Havens |
| 5,370,981 A | 12/1994 | Krafft et al. |
| 5,403,640 A | 4/1995 | Krishnan et al. |
| 5,403,883 A | 4/1995 | Messner et al. |
| 5,447,643 A | 9/1995 | Kelkenberg et al. |
| 5,494,987 A | 2/1996 | Imazato et al. |
| 5,515,117 A | 5/1996 | Dziabo et al. |
| 5,518,788 A | 5/1996 | Invie |
| 5,520,910 A | 5/1996 | Hashimoto et al. |
| 5,536,494 A | 7/1996 | Park |
| 5,536,861 A | 7/1996 | Robertson |
| 5,591,799 A | 1/1997 | Bott et al. |
| 5,608,021 A | 3/1997 | Uchiyama et al. |
| 5,614,538 A * | 3/1997 | Nelson, Jr. .................... 514/345 |
| 5,645,968 A | 7/1997 | Sacripante |
| 5,654,369 A | 8/1997 | Tsubaki et al. |
| 5,700,742 A | 12/1997 | Payne |
| 5,773,507 A | 6/1998 | Incorvia et al. |
| 5,798,048 A | 8/1998 | Ries |
| 5,830,934 A | 11/1998 | Krishnan |
| 5,830,983 A | 11/1998 | Alex et al. |
| 5,834,561 A | 11/1998 | Fukumoto et al. |
| 5,849,822 A | 12/1998 | Kido et al. |
| 5,886,098 A | 3/1999 | Ueda et al. |
| 5,967,714 A | 10/1999 | Ottersbach et al. |
| 5,997,815 A | 12/1999 | Anders et al. |
| 6,022,553 A | 2/2000 | Anders et al. |
| 6,039,940 A | 3/2000 | Perrault et al. |
| 6,045,919 A | 4/2000 | Alex et al. |
| 6,050,979 A | 4/2000 | Haemmerle et al. |
| 6,090,459 A | 7/2000 | Jadamus et al. |
| 6,096,800 A | 8/2000 | Ottersbach et al. |
| 6,103,368 A | 8/2000 | Fukuda et al. |
| 6,127,105 A | 10/2000 | Vandenabeele |
| 6,187,856 B1 | 2/2001 | Incorvia et al. |
| 6,194,530 B1 | 2/2001 | Klesse et al. |
| 6,197,322 B1 | 3/2001 | Dutkiewicz et al. |
| 6,203,856 B1 | 3/2001 | Ottersbach et al. |
| 6,207,361 B1 | 3/2001 | Greener et al. |
| 6,218,492 B1 | 4/2001 | Hill et al. |
| 6,242,526 B1 | 6/2001 | Siddiqui et al. |
| 6,248,811 B1 | 6/2001 | Ottersbach et al. |
| 6,251,967 B1 | 6/2001 | Perichaud et al. |
| 6,266,490 B1 | 7/2001 | Mukai et al. |
| 6,280,509 B1 | 8/2001 | Mallow |
| 6,319,883 B1 | 11/2001 | Graham et al. |
| 6,368,587 B1 | 4/2002 | Anders et al. |
| 6,410,040 B1 | 6/2002 | Melrose et al. |
| 6,428,866 B1 | 8/2002 | Jadamus et al. |
| 6,482,781 B2 | 11/2002 | Graham et al. |
| 6,497,868 B1 | 12/2002 | Tanahashi |
| 6,500,981 B1 | 12/2002 | Weipert |
| 6,525,134 B1 | 2/2003 | Lacroix et al. |
| 6,767,647 B2 | 7/2004 | Swofford et al. |
| 6,797,743 B2 | 9/2004 | McDonald |
| 7,491,753 B2 * | 2/2009 | Krishnan ..................... 523/122 |
| 2001/0007694 A1 | 7/2001 | Ottersbach et al. |
| 2001/0050478 A1 | 12/2001 | Schmitz |
| 2002/0037955 A1 | 3/2002 | Baumann et al. |
| 2002/0081923 A1 | 6/2002 | Artley et al. |
| 2002/0139583 A1 | 10/2002 | Masui et al. |
| 2002/0168473 A1 | 11/2002 | Ottersbach et al. |
| 2002/0177828 A1 | 11/2002 | Batich et al. |
| 2003/0013624 A1 | 1/2003 | Graham et al. |
| 2003/0017194 A1 | 1/2003 | Joerger et al. |
| 2003/0019813 A1 | 1/2003 | Ottersbach et al. |
| 2003/0022576 A1 | 1/2003 | Ottersbach et al. |
| 2003/0049437 A1 | 3/2003 | Devaney et al. |
| 2003/0068440 A1 | 4/2003 | Ottersbach et al. |
| 2005/0003163 A1 | 1/2005 | Krishnan |
| 2005/0065284 A1 | 3/2005 | Krishnan |

FOREIGN PATENT DOCUMENTS

| | | |
|---|---|---|
| DE | 3339662 A1 | 5/1984 |
| DE | 19833062 A1 | 2/2000 |
| EP | 0000426 A1 | 1/1979 |
| EP | 0239213 A2 | 9/1987 |
| EP | 286009 A2 | 10/1988 |
| EP | 0204312 B1 | 8/1990 |
| EP | 0469196 A1 | 2/1992 |
| EP | 0290676 B1 | 8/1994 |
| EP | 747456 A2 | 12/1996 |
| EP | 1109845 | 10/2005 |
| GB | 1299012 | 12/1972 |
| GB | 2091277 A | 7/1982 |
| NL | 7606306 | 12/1976 |
| WO | WO 91/12282 | 2/1991 |
| WO | WO 97/15603 | 5/1997 |
| WO | WO 97/45468 | 12/1997 |
| WO | WO 98/51720 | 1/1998 |
| WO | WO 99/09837 | 3/1999 |
| WO | WO 00/05283 | 2/2000 |
| WO | WO 0008077 | 2/2000 |
| WO | PCT/US2007/018838 | 2/2008 |
| WO | PCT/US2007/018768 | 7/2008 |

OTHER PUBLICATIONS

Michelsen, T., "Building Materials (Survey)," *Kirk-Othmer Encyclopedia of Chemical Technology*, (1992 4$^{th}$ ed.), vol. 4, pp. 618-619.

"Polymer Compositions for Cationic Electrodepositable Coatings," *Journal of Coatings Technology*, vol. 54, No. 686, Mar. 1982.

* cited by examiner

ANTIMICROBIAL AND ANTISTATIC POLYMERS AND METHODS OF USING SUCH POLYMERS ON VARIOUS SUBSTRATES

CROSS-REFERENCE TO RELATED APPLICATIONS

This application is a continuation-in-part of U.S. application Ser. No. 10/882,570, filed Jul. 1, 2004, now U.S. Pat. No. 7,491,753, which claims priority to U.S. Provisional Application Ser. No. 60/484,745 filed Jul. 3, 2003, the contents of each are hereby incorporated by reference.

BACKGROUND OF THE INVENTION

The present invention relates to polymers having inherent antimicrobial or antistatic properties. Such polymers can be applied or used in conjunction with a wide variety of substrates, namely, textiles, metal, cellulosic materials, plastics, and the like to provide the substrate with one or more antimicrobial or antistatic properties. In addition, the polymers can also be combined with other polymers, namely the polymers of the invention can be used as additives to conventional compositions, to provide such other polymers with one or more antimicrobial or antistatic properties.

Various bacteria, fungi, viruses, algae and other microorganisms are known to be in the environment and to potentially adversely affect people coming in contact with them. Such microorganisms are often undesirable as a cause of illness, odors and damage to a wide variety of material and substrates. In order to combat such microorganisms, antimicrobial agents have been suggested. However, there is also a need for such agents to be both sustainable and to be compatible, and to be used on and with a wide variety of polymer materials and substrates.

Various additives and polymer systems have been suggested as providing antimicrobial properties. See, for example, U.S. Pat. No. 3,872,128 to Byck, U.S. Pat. No. 5,024,840 to Blakely et al, U.S. Pat. No. 5,290,894 to Malrose et al, U.S. Pat. Nos. 5,967,714, 6,203,856 and 6,248,811 to Ottersbach et al, U.S. Pat. No. 6,194,530 to Klasse et al. and U.S. Pat. No. 6,242,526 to Siddiqui et al.

With respect to antistatic properties, various substrates tend to accumulate static electrical charge due to low electrical conductivity. This is particularly problematic with plastic substrates. Such accumulation can adversely affect processing, cause electrical damage, such as, for example, in semiconductor devices, provide a fire hazard through the formation of an electrical arc, and exposes personnel handling the substrate to electrical shock. Such effects related to static charge buildup can also have undesirable consequences in personal care applications used on skin and hair, for example flyaways and frizz in hair treated with shampoos. Various solutions to such static buildup have been suggested. See, for example, U.S. Pat. Nos. 4,029,694 and 4,093676 to Weipert et al, 4,098,842 to Login, 4,857,590 to Gaggar et al. and 4,859,727 to Sasaki et al.

There, however, remains a need for potentially safer and less irritating polymer compositions that provide sustainable antimicrobial and/or antistatic properties to a wide variety of substrates and materials.

SUMMARY OF THE INVENTION

The present invention relates to a substrate having one or more antimicrobial or antistatic properties. Such properties are imparted by applying a coating or film formed from a cationically-charged polymer composition comprising a noncationic ethylenically unsaturated monomer, an ethylenically unsaturated monomer capable of providing a cationic charge to the polymer composition, and, optionally, a steric stabilization component incorporated into the cationically-charged polymer composition.

The present invention also relates to a personal care product and polymeric material comprising a base polymer blended with a cationically-charged polymer composition comprising a noncationic ethylenically unsaturated monomer, an ethylenically unsaturated cationic monomer capable of providing a cationic charge to the polymer composition, and, optionally, a steric stabilization component incorporated into the cationically-charged polymer composition.

The present invention also relates to latex compositions comprising a noncationic ethylenically unsaturated monomer, an ethylenically unsaturated cationic monomer capable of providing a cationic charge to the polymer composition, and, optionally, a steric stabilization component incorporated into the cationically-charged polymer composition. A variety of personal care products and disinfectants may comprise the latex composition.

The present invention also relates to a disinfectant composition comprising a cationically-charged polymer composition or latex composition comprising a noncationic ethylenically unsaturated monomer; an ethylenically unsaturated monomer capable of providing a cationic charge to the polymer composition. The disinfectant may, optionally, comprise a steric stabilization component incorporated into the cationically-charged polymer composition. The disinfectant can further comprise at least one active component such as a natural plant-based wax, animal derived wax, natural mineral wax, synthetic mineral wax, synthetic wax, an alcohol comprising a carbon chain length of greater than one, an ester of an alcohol, metal stearate, carboxylic acid, fatty acid, oil, fatty amide, cosmeceutical or nutraceutical.

The present invention also relates to a method of providing one or more antimicrobial or antistatic properties to a substrate. The method includes the step of applying the cationically-charged polymer composition described above to a substrate.

The present invention also relates to a method of imparting one or more antimicrobial or antistatic properties to a polymer material. The method includes the step of blending a base polymer with the cationically-charged polymer composition described above.

DETAILED DESCRIPTION OF THE INVENTION

In the following detailed description, embodiments of the present invention are described in detail to enable practice of the invention. Although the invention is described with reference to these specific embodiments, it is understood that the invention is not limited to these embodiments. The invention includes numerous alternatives, modifications, and equivalents as will become apparent from consideration of the following detailed description.

As used herein, the phrase "active component" includes organic and inorganic components and should be construed in broad terms as an additive that provides a desired end benefit. As one example, an active ingredient of the present invention includes but is not limited to one or more bioactive components that impart antimicrobial, antibacterial, antifungal, antiviral, or antiparasitic activity. As another example, an active ingredient of the present invention includes but is not limited to one or more moisturizing, anti-aging, UV filters, tanning, or anti-dandruff agents.

As summarized above, the present invention utilizes a cationically-charged polymer composition to impart or provide antimicrobial and/or antistatic properties to a substrate or to be blended with a base polymer to provide a polymer material having antimicrobial and/or antistatic properties. The cationically-charged polymer composition includes a noncationic ethylenically unsaturated monomer an ethylenically unsaturated monomer capable of providing a cationic charge to the polymer composition, and, optionally, a steric stabilization component.

Suitable substrates include, but are not limited to fabrics (both woven and nonwoven), organic and inorganic particulates, fibers and agglomerates; foams; films; cellulosic material, including, but not limited to, paper or wood; metal; concrete; masonry; glass; and plastics, both thermoset and thermoplastic and organic substrates like skin and hair.

Various noncationic ethylenically unsaturated monomers may be used in the composition. Examples of monomers can be found in U.S. patent application Ser. No. 09/370,395 filed Aug. 6, 1999 and U.S. Pat. No. 5,830,934 to Krishnan, the disclosures of which are incorporated herein by reference in their entirety. Such monomers include, but are not limited to, vinyl aromatic monomers, such as styrene, para methyl styrene, chloromethyl styrene, vinyl toluene; olefins, such as, ethylene; aliphatic conjugated diene monomers, such as butadiene; non-aromatic unsaturated mono- or dicarboxylic ester monomers, such as methyl methacrylate, ethyl acrylate, butyl acrylate, butyl methacrylate, glycidyl methacrylate, isodecyl acrylate, lauryl acrylate; monomers based on the half ester of an unsaturated dicarboxylic acid monomer, such as monomethyl maleate; unsaturated mono- or dicarboxylic acid monomers and derivatives thereof, such as itaconic acid; nitrogen-containing monomers, such as acrylonitrile, methacrylonitrile, acrylamide, methacrylamide, N-methylol acrylamide, N-(isobutoxymethyl)acrylamide; phosphorus-containing monomers; sulfur-containing monomers, such as styrene sulfonate; and vinyl ester monomers which includes branched vinyl esters, such as vinyl neodecanoate and vinyl versatates.

Fluorinated analogs of alkyl acrylates or methacrylates may also be used. Mixtures of the above may be used.

The composition preferably comprises from about 20 to about 99 percent of the noncationic ethylenically unsaturated monomer based on the total monomer weight.

The composition also includes an ethylenically unsaturated cationic monomer capable of providing a cationic charge to the polymer composition. The cationic monomer is incorporated into the polymer composition by virtue of its ethylenic unsaturation. For the purposes of the invention, the term "cationic monomer" refers to any monomer which possesses or can be altered to provide a net positive charge. For example, this positive charge may be imparted by a heteroatom which is present in the monomer. Exemplary heteroatoms include, but are not limited to, nitrogen, sulfur, and phosphorus.

Examples of cationic monomers include amine and amide monomers, and quaternary amine monomers. Amine and amide monomers include, but are not limited to: dimethylaminoethyl acrylate; diethylaminoethyl acrylate; dimethyl aminoethyl methacrylate; diethylaminoethyl methacrylate; tertiary butylaminoethyl methacrylate; N,N-dimethyl acrylamide; N,N-dimethylaminopropyl acrylamide; acryloyl morpholine; N-isopropyl acrylamide; N,N-diethyl acrylamide; dimethyl aminoethyl vinyl ether; 2-methyl-1-vinyl imidazole; N,N-dimethylaminopropyl methacrylamide; vinyl pyridine; vinyl benzyl amine methyl chloride quarternary; dimethylaminoethyl methacrylate methyl chloride quaternary: diallyldimethylammonium chloride; N,N-dimethylaminopropyl acrylamide methyl chloride quaternary; trimethyl-(vinyloxyethyl) ammonium chloride; 1-vinyl-2,3-dimethylimidazolinium chloride; vinyl benzyl amine hydrochloride; vinyl pyridinium hydrochloride; and mixtures thereof.

Quaternary amine monomers which may be used in the composition of the invention can include those obtained from the above amine monomers such as by protonation using an acid or via an alkylation reaction using an alkyl halide or alkyl sulfate.

Alternatively, the ethylenically unsaturated monomer capable of providing a cationic charge comprises a quaternary derivative capable of providing hydrophobicity. In a preferred embodiment, the quaternary derivative is based on an alkyl group having two to twenty carbons ($C_2$ to $C_{20}$). For example, one could use:

1. $CH_2=C(R)COOCH(OH)CH_2N+(X—)(RO)$ where R=H, $CH_3$ and R=$(CH_2)_nCH_3$ or $(CF_2)CF_3$ and X=Cl, Br, I or a sulfate. For example, this could be a reaction product of glycidyl methacrylate and a secondary amine which has then been quaternized.

2. $CH_2=C(R)KCH_2N+(X)(R)$ where R, R and X have the same significance as above. This is a similar reaction as compared to the one above with vinyl benzyl chloride as the starting material.

3. The third approach could be to start with vinyl pyridine and make the alkyl pyridinium salts as above.

Amine salts can also be used and are obtained, for example, by the reaction of an epoxy group with a secondary amine and subsequent neutralization of the newly formed tertiary amine with an acid. An example of this is the reaction product of glycidyl methacrylate with a secondary amine that can be free radically polymerized.

Quaternary amine functionality can also be generated as a post reaction on a preformed polymer having, for example, an epoxy group. Examples of these kinds of reactions are described in the article, "Polymer Compositions for Cationic Electrodepositable Coatings, *Journal of Coatings Technology*, Vol 54, No 686, March 1982. It should also be appreciated that cationic functionality can also be imparted via sulfonium or phosphonium chemistry, examples of which are also described in the above article.

The composition preferably comprises from about 0.5 to about 98 percent of the ethylenically unsaturated monomer capable of providing a cationic charge based on the total monomer weight, the amount depending on the selected application of the polymer composition.

The composition also, optionally, comprises a component which is incorporated into the cationically-charged polymer, composition to sterically stabilize the composition. Suitable components include, but are not limited to, monomers, polymers, and mixtures thereof as set forth below. For the purposes of the invention, the term "incorporated" with respect to the use of the monomer can be interpreted to mean that the monomer attaches to the backbone of the cationic polymer. The polymer which is "incorporated" into the composition can be interpreted to mean that it is adsorbed or grafted onto the composition surface, an example of which may be polyvinyl alcohol. This stabilizing component may encompass a nonionic monomer or polymer which incorporates steric stabilization to the composition particle without adversely affecting the polymer composition. Exemplary monomers that can be used as steric stabilizers include, but are not limited to, those which contain alkoxylated, including, but not limited to, ethoxylated or propoxylated, functionality. Examples of such monomers include those described by the formulas:

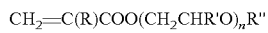

where R=H, $C_1$-$C_4$ alkyl; and R'=H, $C_1$-$C_4$ alkyl, and R"=H, $C_1$-$C_{12}$ alkyl, and n=1-30; or $CH_2$=C(R)COO $(CH_2CH_2O)_n(CH_2CHR'O)_mR'''$—where R=H, $C_1$-$C_4$ alkyl, and R'=H, $C_1$-$C_4$ alkyl, and R"=H, $C_1$-$C_{12}$ alkyl, n and m each may range from 1-15; and

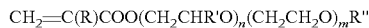

where R=H, $C_1$-$C_4$ alkyl, and R'=H, $C_1$-$C_4$ alkyl and R"=H, $C_1$-$C_{12}$ alkyl, n and m=1-15.

Preferred compounds are undecylenic acid esters where R" is $C_{11}$. Preferably, the monomers have a molecular weight of less than 2000.

Ethoxylated mono- and diesters of diacids such as maleic and itaconic acids can also be used to achieve the same stabilizing effect.

The composition can further comprise at least one surfactant. Suitable surfactants include, but are not limited to, cationic surfactants, nonionic surfactants, anionic surfactants, amphoteric surfactants or a mixture of these surfactants. In one embodiment, polymerizable surfactants based on acrylate, methacrylate, vinyl, and allyl versions of surfactants can be used. An example of this is TREM LF-40 sold by Henkel of Düsseldorf, Germany. These surfactants possess ethylenic unsaturation that allows the surfactants to be incorporated into the polymer composition. Similar to other surfactants, these materials have hydrophobic and hydrophilic functionality that varies. Surfactants that are particularly applicable to the present invention are nonionic surfactants wherein the hydrophilic character is believed to be attributable to the presence of alkylene oxide groups, such as ethylene oxide, propylene oxide, butylene oxide, and the like. Block copolymers of ethylene oxide and/or propylene oxide such as the Pluronic or Tetronic series from BASF can also be used, particularly in antistatic applications. The degree of hydrophilicity can vary based on the selection of functionality.

Polymers can also be used to provide steric stability. For example, protective colloids may be used. Examples of these materials include, but are not limited to, polyvinyl alcohols, polyvinyl pyrollidone, hydroxyethyl cellulose, polyethylene glycols, polyglycol-ethers, propylene glycols, ethylene oxide/propylene oxide copolymers, ethylene oxide/propylene oxide copolymers and/or ethylene oxide/butylene oxide copolymers and the like. Mixtures of any of the above monomers and polymers may also be used. Other monomers and polymers which may be used to impart stability are listed in U.S. Pat. No. 5,830,934 to Krishnan et al.

The steric stabilization component which is optionally used to stabilize the composition is present in an amount ranging from about 0 to about 75 percent based on the total weight of the monomers.

The composition of the invention also may include a free radical initiator, the selection of which is known in the art. Preferably, a free radical initiator is used which generates a cationic species upon decomposition and contributes to the cationic charge of the composition. An example of such an initiator is 2,2'-azobis(2-amidinopropane) dihydrochloride) sold commercially as Wako V-50 by Wako Chemicals of Richmond, Va.

The composition of the invention may also include other additives to improve the physical and/or mechanical properties of the polymer, the selection of which are known to one skilled in the art. These additives include processing aids and performance aids such as, but are not limited to, crosslinking agents, natural and synthetic binders, plasticizers, softeners, foam-inhibiting agents, froth aids, flame retardants, dispersing agents, pH-adjusting components, sequestering or chelating agents, and other components. In one embodiment, 0.1 to 1.0 weight percent of a nonionic surfactant can optionally be used during the polymerization process. Additionally, the composition preferably can be devoid of conventional non-polymerizable cationic and anionic surfactants.

The composition may be applied to the substrate as a coating or film using techniques known to those skilled in the art such as spraying, roll-coating, brushing, dipping, impregnation, size press and the like.

The composition of the present invention can be blended with a base polymer including other polymers. Suitable base polymers include various thermoplastic and thermosetting polymers including, but not limited to polyurethanes, phenolics, polyesters, polyolefins, polyamides, polycarbonates, polyethers, polyether-amides and imides, polyorganosilanes, polysulfones, polyisoprene, polychloroprene, acrylics, styrene-butadienes, styrene acrylonitriles, ABS, EVA, polytetrafluoroethylene, polyether-esters, polyepoxides, heterocyclic polymers such as polypyrrole, polyaniline, polythiophene and its derivatives and the like and latex-based materials. In another embodiment, the cationically-charged polymer can be blended with another polymer having antimicrobial or antistatic properties such as other cationic polymers.

The blends could be made in situ creating an interpenetrating polymer network (IPN). Core shell latices or composites could be made that have one or more of these above mentioned components as a core on which subsequent polymerization could take place by an emulsion or suspension process. Another example of this would be making the polymers, such as, for example urethanes, starting from the base raw materials by a suspension or dispersion/miniemulsion process followed by a radical process. Thus, one could combine a condensation and a free radical process together. The objective would be to make a broader range of polymers that are hybrids. Another enhancement of the chemistry could come from using controlled radical polymerization processes such as RAFT, ATRP, and SFRP (with nitroxides) which would then provide polymers that would have a variety of architectures such as block, graft, stars, hyperbranched and dendrimers. This allows control of the morphology, activity, and uniqueness of the polymers and enables one to create molecules tailored to meet specific functions.

The composition can be used in the form of an open or closed cell foam by adding surfactants and foaming agents. The foam can be used in a wide variety of ways so as to impart antimicrobial and/or antistatic properties to various articles. For example, a foam could be used to provide both sound deadening properties and one or more of antimicrobial or antistatic properties to an article like the foam underlay of a carpet. The foam could be used as the article itself, for example, the foam of a pillow or mattress. The foam could be used as an absorbent in a diaper thereby absorbing the urine while providing antimicrobial protection, or as a wipe or towellette in a personal care application.

Amphoteric or zwitterionic polymers in which an anionic monomer or polymer would be included could also be made using the composition of the present invention.

Antimicrobial and/or antistatic agents may be used as an additive to enhance the inherent antimicrobial or antistatic nature of the compositions of the present invention. A potential antimicrobial monomer is undecylenic acid or alcohol or reaction products of undecylenic acid or alcohol with hydroxyl or acid containing materials having ethylenic unsaturation to produce an ester. An example of the acid functional monomer is acrylic acid or maleic anhydride. An example of the hydroxyl functional monomer is hydroxylethyl methacrylate or polyethylene glycol methacrylate. Undecylenic acid is known to provide antifungal properties and this could potentially offer advantages again in expanding the chemistry especially if combined with the cationic and phenolic type intermediates.

Chitosan, modified chitosans or chitosan salts can also be incorporated into the composition. Chitosan is a naturally occurring amino functional saccharide which is known to be antimicrobial. Moreover, chitosan could also serve the dual purpose of also providing steric stabilization.

Other antimicrobial agents include metal biocides such as silver, zinc, etc. and salts and oxides thereof, chlorhexidine, chlorhexidine gluconate, glutaral, halazone, hexachlorophene, nitrofurazone, nitromersol, povidone-iodine, thimerosol, $C_1$-$C_5$-parabens, hypochlorite salts, clofucarban, clorophene, poloxamer-iodine, phenolics, mafenide acetate, aminacrine hydrochloride, quaternary ammonium salts, oxychlorosene, metabromsalan, merbromin, dibromsalan, glyceryl laurate, sodium and/or zinc pyrithione, (dodecyl) (diethylenediamine) glycine and/or (dodecyl) (aminopropyl) glycine; phenolic compounds including, but not limited to, phenols, m-cresol, o-cresol, p-cresol, o-phenyl-phenol, resorcinol, vinyl phenol, and the like, polymeric guanidines, olymyxins, bacitracin, circulin, the octapeptins, lysozmye, lysostaphin, cellulytic enzymes generally, vancomycin, ristocetin, the actinoidins and avoparcins, tyrocidin A, gramicidin S, polyoxin D, tunicamycin, neomycin, streptomycin and the like. This list is not intended to provide an exhaustive list of potentially useful antimicrobials. Rather, incorporation by reference is made to several references: "Antibiotics, Chemotherapeutics, and Antibacterial Agents for Disease Control," M. Grayson, Ed., J. Wiley and Sons, N.Y., 1982; classification of antibiotics by their mode of action may be found in "The Molecular Basis of antibiotic Action," Second Edition, E. F. Gale et al., J. Wiley and sons, N.Y., 1981; additives and polymer systems are described in U.S. Pat. No. 3,872,128 to Byck, U.S. Pat. No. 5,024,840 to Blakely et al, U.S. Pat. No. 5,290,894 to Malrose et al, U.S. Pat. Nos. 5,967,714, 6,203,856 and 6,248,811 to Ottersbach et al, U.S. Pat. No. 6,194,530 to Klasse et al. and U.S. Pat. No. 6,242,526 to Siddiqui et al., the disclosures of each are incorporated by reference in their entirety.

Antistatic agents include nitrogen compounds such as long chain amines, amides and quaternary ammonium salts, esters of fatty acids and their derivatives, polyhydric alcohols and their derivatives, phosphoric acid derivatives, solutions of electrolytes in liquids with high dielectric constants, metallic salts and oxides, metals (e.g., iron), carbon black, carbon nanotubes and semiconductors. Specific examples include Hostenstat® and Sandin® antistats from Clariant, Larostat® antistats from BASF, Bayhydrol® antistats from Bayer, Atmer® antistats from Uniquema, VersaTL® from Alco, and various other antistats offered by Atofina, Noveon, Ciba, Eastman, Agfa, Ormecon Chemie and Panipol.

With respect to providing antistatic compositions, the reaction products of alkyl amines or ethoxylated amines with maleic anhydride could also be used. This could lead to a maleimide-type monomer with ethoxylate or alkyl chains that could be copolymerized with other monomers. Copolymers of alkylene oxide macromers and other monomers such as styrene sulfonates, acrylamidopropane sulfonic acid (AMPS) carboxylic acids, (e.g., acrylic or methacrylic derivatives) are potential antistatic additives. Other antistatic solutions are suggested in U.S. Pat. Nos. 4,029,694 and 4,093,676 to Weipert et al, 4,098,842 to Login, 4,857,590 to Gaggar et al. and 4,859,727 to Sasaki et al., the disclosures of which are incorporated by reference in their entirety.

In a further aspect of the present invention, at least one active component can be post-added to the substrate, polymeric material or latex composition or formulation described herein. The active component can be a hydrophobic component such as natural plant-based waxes, animal derived waxes, natural and synthetic mineral waxes and synthetic waxes such as paraffin, carnauba, ozocertie, montan wax, polyolefin waxes, such as, for example, polybutylene, beeswax, or lanolin, candelilla and carnauba wax; alcohols comprising a carbon chain length of greater than one, preferably greater than four carbons, especially fatty alcohols such as cetyl alcohol, stearyl alcohol, cetostearyl alcohol, behenyl alcohol, propylene glycols, myristyl alcohols, arachidyl alcohol, lignoceryl alcohol; esters of the aforementioned alcohols such as stearates and myristates; metal stearates such as calcium stearate, zinc stearate, magnesium stearate or barium stearate; carboxylic acids such as caprylic acid, pelargonic acid, capric acid, undecylic acid, lauric acid, palmitic acid, behenic acid, terephthalic acid, phthalic acid, isophthalic acid, naphthalene-2,6-dicarboxylic acid, cyclohexanedicarboxylic acid, cyclohexanediacetic acid, succinic acid, adipic acid, and sebacic acid, especially carboxylic acids having a chain length greater than three carbons; fatty acids such as stearic acid, oleic acid, undecylenic acid and linoleic acid; oils such as perfume oils, essential oils, vegetable oil, fish oil, paraffin oil and mineral oil; fatty amides including primary amides such as stearamide, oleamide, erucamide, secondary amides such as stearyl stearamide, stearyl erucamide, bis amides such as ethylene bis stearamide, ethylene bis oleamide, alkanolamides such as coco mono ethanolamide, coco diethanolamide, oleic diethanolamide, lauric diethanolamide and stearic diethanoiamide, as well as other various fatty amides such as aprylamide, pelargonamide, capramide, lauramide, myristamide, palmitamide, stearamide, arachidamide, behenamide, stearyl stearamide, palmitoleamide, oleamide, erucamide, linoleamide, linolenamide, oleyl palmitamide, stearyl erucamide, erucyl erucamide, oleyl oleamide, erucyl stearamide, and ricinoleamide; fatty bisamides such as ethylenebisstearamide, ethylenebisoleamide and ethylenebis 12-hydroxystearamide or any combination thereof. The cationically-charged polymer composition could also be used as an additive in the solid form to be added to specific substrates and then processed. In the case where the solid is to be used it would be added to the base polymer during the processing stage, e.g., as pellets into polycarbonate or SAN before extrusion or injection molding. In this case, the composition of our invention would become the integral part of the article as opposed to a topical coating on the surface. The polymers can be made in the solid form via a variety of suitable polymerization methods including bulk, solution, thermal emulsion, suspension, ultra-violet (UV)-initiated bulk, and UV-initiated on-web polymerization techniques. Preferably, the polymers are made in the solid form either by spray drying a dispersion/emulsion or by making it directly as a solid by suspension polymerization.

In another aspect of the present invention, the at least one active component can be a cosmeceutical or nutraceutical ingredient. For example, the active component may be a moisturizing or anti-wrinkle/anti-aging agent ingredient such as glycerin, propylene glycol, polyethylene glycol, hyaluronic acid, chondroitin sulfate, elastin, collagen, polysaccharide, glycosaminoglycan, ascorbic acid, ascorbic acid derivatives, glucosamine ascorbate, arginine ascorbate, lysine or tyrosine ascorbate, gluthathione ascorbate, nicotinamide ascorbate, niacin ascorbate, allantoin ascorbate, creatine ascorbate, creatinine ascorbate, chondroitin ascorbate, chitosan ascorbate, DNA ascorbate, carnosine ascorbate, tocotrienol, rutin, quercetin, hesperedin, diosmin, mangiferin, mangostin, cyanidin, astaxanthin, lutein, lycopene, resveratrol, tetrahydrocurcumin, rosmarinic acid, hypericin, ellagic acid, chlorogenic acid, oleuropein, alpha-lipoic acid, niacinamide lipoate, gluthathione, andrographolide, carnosine, niacinamide, polyphenols, pycnogenol and mixtures thereof; UV blocker and absorber ingredients (sunscreen) such as benzophenones, benzotriazoles, homosalates, alkyl cinnamates, salicylates such as octyl salicylate, dibenzoylmethanes, anthranilates, methylbenzylidenes, octyl triazones, 2-phenylbenzimidazole-5-sulfonic acid, octocrylene, triazines, cinnamates, cyanoacrylates, dicyano ethylenes, etocrilene, drometrizole trisiloxane, bisethylhexyloxyphenol methoxyphenol triazine, drometrizole, dioctyl butamido triazone, terephthalylidene dicamphor sulfonic acid and para-aminobenzoates as well as ester derivatives thereof; antiacne agents such as salicylic acid; anti-dandruff agents such as zinc pyrithione; skin bronzing or tanning agent ingredients such as dihydroxyacetone, erytrulose, melanin; antioxidants such as vitamin C and derivatives thereof (e.g. ascorbyl acetate, ascorbyl phosphate and ascorbyl palmitate), vitamin A and derivatives thereof; folic acid and derivatives thereof; vitamin E and derivatives thereof such as tocopheryl acetate, flavons, or flavonoids, amino acids such as histidine, glycine, tyrosine, tryptophan, and derivatives thereof; carotenoids and carotenes; uric acid and derivatives thereof; citric acid, lactic acid, malic acid; stilbenes and derivatives thereof; and pomegranate extracts; vitamin K1 or K2, vitamin K1 oxide or vitamin K2 oxide, hormones, minerals, plant or botanical extracts, anti-inflammatory agents, concentrates of plant extracts, emollients, skin protectants, humectants, silicones, skin soothing ingredients, analgesics or anti-itch agents, skin penetration enhancers, solubilizers, alkaloids and processing aids; coloring agents including various dyes and pigments; and perfumes or fragrances for the body; or any combination thereof.

The at least one active component can be a free radical scavenger such as cuprous halide, cupric halide, cupric acetate, cupric formate, cuprous acetate, cuprous formate, ferrous halide, ferric halide, ferrous sulfate, ferric sulfate, cysteine, glutathione, N-acetylcysteine, L-alpha-acetamido-beta mercaptopropionic acid, S-nitroso-glutathione, N-acetyl-3-mercapto-alanine, butylated hydroxyanisole, butylated hydroxytoluene, L-2-oxothiazolidine-4-carboxylate, desferrioxamine, allopurinol, superoxide dismutase and salen-manganese complexes; and any combination thereof.

In one embodiment of the present invention, a disinfectant composition can be prepared comprising a cationically-charged polymer composition comprising a noncationic ethylenically unsaturated monomer; an ethylenically unsaturated monomer capable of providing a cationic charge to the polymer composition; and, optionally, a steric stabilization component incorporated into the cationically-charged polymer composition as defined herein. The disinfectant can further comprise at least one active component such as a natural plant-based wax, animal derived wax, natural mineral wax, synthetic mineral wax, synthetic wax, an alcohol comprising a carbon chain length of greater than one, an ester of an alcohol, metal stearate, carboxylic acid, fatty acid, oil, fatty amide, cosmeceutical or nutraceutical.

The disinfectant composition can further comprise a variety of common disinfecting compounds such as, for example, quaternary ammonium compounds, phenols and alcohols as well as any surfactants or solvents used for household cleaning including glycol ethers, alcohols, chlorinated solvents such as methylene chloride, and petroleum derivative solvents. Inorganic detergent builders such as phosphates, silicates, carbonates and zeolites may also be added. When combined, the disinfecting compounds may provide short-term disinfectant activity while the cationically-charged polymer composition may provide long-term disinfectant activity. The pH of the disinfectant composition can be less than or equal to 4 or greater than or equal to 9.

As summarized above, the present invention includes a latex composition that may comprise a noncationic ethylenically unsaturated monomer; an ethylenically unsaturated monomer capable of providing a cationic charge to the polymer composition; and, optionally, a steric stabilization component incorporated into the cationically-charged polymer composition as disclosed herein. The ethylenically unsaturated monomer capable of providing a cationic charge to the polymer composition may comprise a quaternized amine monomer or a quaternary derivative capable of providing hydrophobicity to the polymer composition or a combination thereof. The steric stabilization component can be a polymerizable surfactant, a monomer having alkoxylated functionality or is a protective colloid. The monomer having alkoxylated functionality is (a) $CH_2\!\!=\!\!C(R)COO(CH_2CHR'O)_nR''$— where R=H, $C_1$-$C_4$ alkyl; and R'=H, $C_1$-$C_4$ alkyl, and R''=H, $C_1$-$C_{12}$ alkyl, and n=1-30; or $CH_2\!\!=\!\!C(R)COO(CH_2CH_2O)_n(CH_2CHR'O)_mR''$—where R=H, $C_1$-$C_4$ alkyl, and R'=H, $C_1$-$C_4$ alkyl, and R''=H, $C_1$-$C_{12}$ alkyl, n and m each may range from 1-15; and $CH_2\!\!=\!\!C(R)COO(CH_2CHR'O)_n(CH_2CH_2O)_mR''$—where R=H, $C_1$-$C_4$ alkyl, and R'=H, $C_1$-$C_4$ alkyl and R''=H, $C_1$-$C_{12}$ alkyl, n and m=1-15, or (d) mixtures of (a) and (b).

The latex composition can include up to about 1.0 weight percent of at least one surfactant. The at least one surfactant is a cationic surfactant, nonionic surfactant, anionic surfactant, amphoteric surfactant, or a mixture thereof.

The latex composition can further include an antimicrobial agent or antistatic agent such as a chitosan-based material or a metal biocide such as silver and zinc, and salts or oxides thereof, as well as undecylenic acid or alcohol or a reaction product of undecylenic acid with hydroxyl or acid containing material having ethylenic unsaturation. The antistatic agent can be at least one nitrogen compound chosen from esters of fatty acids, polyhydric alcohols, phosphoric acid derivatives, solutions of electrolytes in liquids with high dielectric constants, metal salts and oxides, metals, carbon black, carbon nanotubes or semiconductors.

The latex composition may further comprise at least one active component chosen from natural plant-based wax, animal derived wax, natural mineral wax, synthetic mineral wax, synthetic wax, an alcohol comprising a carbon chain length of greater than one, an ester of an alcohol, metal stearate, carboxylic acid, fatty acid, oil, fatty amide, cosmeceutical or nutraceutical.

The polymeric materials and latex compositions of the present invention may also include various additives including at least one inorganic component. The at least one inorganic component may be an inorganic pigment including, but not limited to, titanium dioxide or zinc oxide; black pigments, such as iron oxide black; fancy or multi-colored pigments, such as ultramarine or iron oxide red; lustrous pigments, metal effect pigments, pearlescent pigments as well as fluorescence or phosphorescent pigments; metal oxides, metal hydroxides and metal oxide hydrates, mixed phase pigments, sulfur-containing silicates, metal sulfides, complex metallocyanides, metal sulfates, metal chromates, metal molybdates, yellow iron oxide, brown iron oxide, manganese violet, sodium aluminum sulfosilicate, chromium oxide hydrate, ferric ferrocyanide, and cochineal. The inorganic component can also be at least one inorganic solids such as seed, broken seed nut shells, beads, luffa particles, polyethylene balls, clay, calcium bentonite, kaolin, china clay, talc, perlite, mica, vermiculite, silicas, quartz powder, montmorillonite, calcium carbonate, a talc or a member of the mica family or a chemical equivalent thereof. Still further, the at least one active component can be a nano-inorganic material such as nano clays, nano oxides, nanotubes, or the like. Further, although implied, the present invention includes any combination thereof.

It is possible to conceive ways by which the polymeric materials and latex compositions of our invention can be directly incorporated into a fiber while it is being processed. One way is during the melt spinning/extrusion of the fibers. The additive could be added directly to the polymer used for fiber making e.g., polyolefins, polyester, acrylic etc during the processing stage or could be pre-compounded into a master batch with the polymer and other ingredients and mixed thoroughly before addition to the fiber making polymer. This way the composition is mixed thoroughly before addition to the fiber making polymer. This way the composition would be directly extruded or be part of the fiber and impart its antimicrobial or antistatic properties. This would apply to any polymer that can be melt spun and the additive can be designed to impart compatibility, hydrophilicity, and flexibility to the fiber in addition to the stated properties for which it was designed. These fibers then could be used for many applications some of which have been outlined above. Solution spinning of fibers could also be considered in which case the additive would be dissolved in the fiber spinning solution and then extruded through spinnerets.

Another area which would benefit from the solid additive processing is plastics and rubber articles. Here again, one could conceive of adding the composition polymer, which would serve as a thermoplastic additive, as powder or pellets directly during the processing step such as extrusion, injection molding etc or could be pelletized prior to actually processing in a compatibilizing polymer such as EVA and EMA using the extruder and added to any thermoplastic polymer in specific amounts during a post processing step using the extruder, injection molding machine, blow molding, or other similar technique. Typical plastic processing steps for thermoplastic polymers would be compatible with these solid additives. Also, the additive can be mixed along with other ingredients such as pigments, flow aids, lubricants, or one or more suitable surfactants including, but not limited to, cationic surfactants, nonionic surfactants, anionic surfactants, amphoteric surfactants or a mixture of these surfactants or other additives well known in the art, with the desired polymer to make what are known as master batches. These master batches would typically be made in high shear mixing equipment such as a Banbury mixer and the mix would then be pelletized in an extruder. The master batches would then be processed by the manufacturer of plastic articles or films using conventional plastic processing equipment. Any or all of the above methods could be used to deliver the additive into a matrix polymer for providing the desired antimicrobial and/or antistatic property. Once again the applications would be similar to the ones outlined above. The dry polymer could be added to thermoset polymer also, such as phenolics, epoxies, or the like, and processed using techniques such as compression molding. The additive processing techniques for rubber would be similar in terms of making a rubber compound using a Banbury and then made into sheets, for example, through a two roll mill or extruded into tubes, pipes, hoses, or the like.

One specific application could be in the area of artificial or synthetic marble surfaces made of acrylic polymers, such as, for example, Corian® surface material or unsaturated polyesters. The polymer additive could be compounded into these resins and then cast or cured to incorporate it into the matrix. This would permanently incorporate the additive into the matrix instead of a topical coating. The same could be for the use of these additives in gel coats and casting resins used in boats etc to provide surfaces with the described properties. If an unsaturated polyester resin were used, it would be preferable to dissolve the additive in styrene.

Another example for solids would be use of these as additives in hot melt adhesive compositions to create adhesives that have the described attributes. The polymer would have to have the required compatibility and molecular weight to provide adequate flow.

In the case of cellulosic materials, the use of solid materials can be envisaged in composites made from wood where the wood in granular, pelletized, or powder form could be compounded with other ingredients and then molded into a shape by techniques such as compression molding. Thermosetting resins such as UF, MF, epoxy, and urethane resins are used for bonding wood and the polymer composition could be added along with these during the processing stage. Applications such as decking and construction materials and OSB boards could be considered using this approach.

The use of solid material in paper can be considered in the making of high-pressure laminate or decorative laminates and molded articles. Once again the solid material can be combined with pulp fibers and fillers and compression molded to make the finished product. Packaging materials such as cartons, boxes, and the like could also benefit from the practice of the present invention.

The cationically-charged polymer composition in dry form can be combined with cement/concrete and set to form a concrete structure that has the desired addendum properties. Grouts, sealers, mastics, and the like would also be amenable to the use of powders. This can also be combined with other fillers to make counter tops, floors and other building materials that have one or more antimicrobial or antistatic properties. Redispersible powders in cement would be another use and in decorative concrete.

The composition of the present invention should also be used in combination with other methods and formulations for improving one or more antimicrobial or antistatic properties such as described in U.S. Pat. No. 3,872,128 to Byck, U.S. Pat. No. 5,024,840 to Blakely et al, U.S. Pat. No. 5,290,894 to Malrose et al, U.S. Pat. Nos. 5,967,714, 6,203,856 and 6,248,811 to Ottersbach et al, U.S. Pat. No. 6,194,530 to Klasse et al., U.S. Pat. No. 6,242,526 to Siddiqui et al., U.S. Pat. No. 4,029,694 and U.S. Pat. No. 4,093,676 to Weipert et al, U.S. Pat. No. 4,098,842 to Login, U.S. Pat. No. 4,857,590 to Gaggar et al., and U.S. Pat. No. 4,859,727 to Sasaki et al; each herein incorporated by reference.

Potential Uses

The composition of the present invention can be applied to a wide variety of substrates using various techniques known to those skilled in the art. The following list is not to be intended as limiting the types of substrates, but rather exemplary of potential uses. For example, the composition as a latex can be applied as a coating or as a film to the following substrates:

1. Nonwoven and Woven Textiles and Fibers: Examples would include natural fibers such as cotton and wool to synthetic fibers such as nylon, acrylics, polyesters, urethanes, and the like. Application process would be through processes such as rod/knife coating, impregnation, back coatings, printing, or as pretreatments on individual fibers or as a finished good.

2. Plastics/Rubber: Examples would include commodity molded thermoplastics like polyolefins to engineering thermoplastics such as polysulfones, acetals, polycarbonates, and the like; thermosets like epoxies, urethanes, and the like; and as extruded or blown films. The polymer would be applied as a coating on the surface by rod/knife coating, spray, dipping, or as a laminate coating during the extrusion process or as a coating applied in the mold during the molding process. Rubber products would include sheets, extruded/molded articles, composites, or other similar articles such as gloves.

3. Paper: This would include both preformed paper and as additives in the wet end process. Typical paper processes would include impregnation or saturation, rod/knife coating etc, size press, and wet end addition, or spray-on.

4. Inorganic/Organic Materials: This would cover a wide range of delivery mechanisms based on encapsulation and coating of inorganic particles including, but not limited to, clay, mica, pigments, biocides, pesticides, and the like, and also as part of a formulation involving a variety of fillers to make a finished product such as, for example, gypsum board, sealer, grout, or the like, or as a coating on an inorganic surface such as a drywall, tiles, and may be applied by spraying, roller coating, brushing, or other application. This would also cover its use in glass fiber mat coating or impregnation.

5. Wood: This would include all kinds of wood substrates both natural and engineered and the application process could be a variety of methods as outlined above.

6. Metal: Again this would encompass both metals and metal alloys, including carbon steel, stainless steel and including solid steel bars, sheets, coils, ropes, or the like wherein the composition is applied as a coating by one of the numerous processes such as spraying dipping, brushing, roller coating, or other application.

Specific applications include textiles such as: residential and commercial carpets, tiles, or other materials; liquid and air filters; HVAC; vacuum cleaners; automotive; medical or surgical gowns, drapes, dressings, covers and other laboratory apparel; pretreatment for fibers, printed and dyed fabrics for apparel, furnishings, sheets, towels, and other textiles; diapers and incontinence articles, interior automotive applications such as trim, upholstery, mats, filters, and the like; upholstery coatings, laminating and bonding adhesives; foams for sound absorbency; foamed articles such as pillows and mattresses; belting; food handling; tapes, including masking tapes, surgical, or industrial tapes; electrical, industrial, and household cleaning wipes, cloths and sponges; shoe products including insoles, box toes, and the like; any traditional application of plastics or rubber such as in tool handles namely, screw drivers, hammers, or shovels; toys, rubber gloves, sheets, articles; machinery housing including computers, display devices, diagnostic devices, vacuum cleaners, and instrumentation; medical devices including, but not limited to catheters, balloons, tubing, syringes, diagnostic kits, and the like; packaging or product protection including perishables, computer peripherals, semiconductors, memory chips, CD's, DVD's or other products; impact modifiers for acrylics, polycarbonates and the like; overdips and underdips for gloves including gloves for clean room, breathable films, antipenetrant for fabric supported gloves; cutting boards; extruded and blown films for packaging; paper: vacuum bags, book covers, air filters, liquid filters, wallcoverings, wet and dry wipes, tissues, or other similar products; felt for vinyl floor coverings, molded pulp applications, packaging including boxes, cartons, molded articles and the like; size press coatings including gift wraps, ink jet media, breathable coatings, and the like; wet end additives in paper, tapes, and labels for masking, surgical, or general purpose; adhesives including tapes, labels, decals, films, book binding, either pressure sensitive or FPLA; shoe insoles, inorganic/organic materials such as coating/encapsulation of fillers and pigments, construction sealers and grouts, gypsum wallboard coatings/paints, exterior/interior coatings; tile adhesives, floor coatings, specifically for hospitals, clean rooms, clinics, schools and other institutional settings; coatings for hospital and medical environments; ceiling tiles, glass fiber coating including glass mats, insulation, reinforced composites; liquid disinfectants and cleaners, personal care products including, but not limited to shampoos, conditioners, lotions, creams, hair and skin care, hair depilatory, body wash, cosmetics, insect repellants, toiletries and the like; hygiene coatings of surfaces other than floors hospitals, clinics, schools, homes and offices, hard and porous surface coatings including walls, ceilings, floors, counter tops and other surfaces; decorative concrete, wood such as oriented strand board (OSB) coatings, decking and construction materials including coating or impregnation; composite construction materials, furniture coatings; hygiene coatings, including table and counter tops, door knobs, or door handles; flooring including laminates, hardwood and other composite floors, decorative laminates including table tops, counter tops, furniture or other similar application; metal such as cabinets, door knobs, handles and the like; furniture, coatings for example appliances, OEM, and the like.

Having generally described the present invention, a further understanding can be obtained by reference to the examples provided herein for purposes of illustration only and are not intended to be limiting.

Examples 1-4 were tested for antimicrobial properties using *Bacillus subtilis* ATCC #6633 as the test organism. Example 3 is an anionic polymer and is a comparative example.

|  | 1 | 2 | 3 | 4 |
|---|---|---|---|---|
| Monomer Composition | | | | |
| Styrene | 54.5 | 47.5 | 55 | 39.5 |
| Butyl acrylate | 13.5 | 13.5 | 0 | 28.5 |
| Butadiene | 20.0 | 20.0 | 43 | 0 |
| Lauryl Methacrylate | 0 | 0 | 0 | 10.0 |
| N-methylolacrylamide | 2.0 | 2.0 | 0 | 2.0 |
| Dimethyl aminoethyl methacrylate methyl chloride quaternary | 5.0 | 12.0 | 0 | 15.0 |
| Monomethyl maleate | | | 2.0 | 0 |
| Surfactants | | | | |
| Abex 2525 | 0.5 | 0.5 | 0.0 | 0.5 |
| Methoxyl polyethylene glycol methacrylate | 5.0 | 5.0 | 0.0 | 5.0 |
| Dowfax 2A1 | | | 1.2 | |

Quanticult® Plus cultures containing 10-100 CFU/0.1 mL were inoculated and allowed to dry onto fifteen coupons for each test coating. Fifteen coupons coated with the negative control coating were inoculated in the same manner. Recovery for each surface type was determined after one hour, four hours and 24 hours, using Rodac plates (TSA containing Tween and Lecithin). At each sample time a Rodac plate was touched to five coupons for each surface type and incubated at 30-35° C. for 48 hrs-5 days. The CFU were counted and averaged for each surface type. The test surface results were compared with the negative control surface results. Recovery <70% indicates that the material is antimicrobial. The results are provided in Tables 1-4.

TABLE 1

(Example 1)

| Replicate | 1 Hour | | 4 Hour | | 24 Hour | |
|---|---|---|---|---|---|---|
| | B. subtilis CFU | Other CFU | B. subtilis CFU | Other CFU | B. subtilis CFU | Other CFU |
| Microbial Recovery | | | | | | |
| 1 | 0 | 2 | 0 | 4 | 0 | 6 |
| 2 | 0 | 9 | 0 | 9 | 0 | 4 |
| 3 | 0 | 20 | 0 | 2 | 0 | 9 |
| 4 | 0 | 24 | 0 | 7 | 0 | 7 |
| 5 | 0 | 31 | 0 | 6 | 0 | 3 |
| Average | 0 | N/A | 0 | N/A | 0 | N/A |
| % Recovery[1,2] | | | | | | |
| N/A | 0 | | 0 | | 0 | |

[1]Percent Recovery calculated using only the B. subtilis CFUs.
[2]Percent Recovery calculated by comparing the average CFU to those of Example 3.

TABLE 2

(Example 2)

| Replicate | 1 Hour | | 4 Hour | | 24 Hour | |
|---|---|---|---|---|---|---|
| | B. subtilis CFU | Other CFU | B. subtilis CFU | Other CFU | B. subtilis CFU | Other CFU |
| 1 | 0 | 0 | 0 | 1 | 0 | 1 |
| 2 | 0 | 0 | 0 | 1 | 0 | 3 |
| 3 | 0 | 0 | 0 | 2 | 0 | 4 |
| 4 | 0 | 0 | 0 | 0 | 0 | 5 |
| 5 | 0 | 1 | 0 | 0 | 0 | 3 |
| Average | 0 | N/A | 0 | N/A | 0 | N/A |
| % Recovery[1,2] | | | | | | |
| N/A | 0 | | 0 | | 0 | |

[1]Percent Recovery calculated using only the B. subtilis CFUs.
[2]Percent Recovery calculated by comparing the average CFU to those of Example 3.

TABLE 3

(Comparative Example 3)

| Replicate | 1 Hour | | 4 Hour | | 24 Hour | |
|---|---|---|---|---|---|---|
| | B. subtilis CFU | Other CFU | B. subtilis CFU | Other CFU | B. subtilis CFU | Other CFU |
| 1 | 1 | 4 | 7 | 12 | 4 | 13 |
| 2 | 3 | 5 | 6 | 2 | 0 | 10 |
| 3 | 2 | 2 | 5 | 5 | 0 | 9 |
| 4 | 2 | 3 | 1 | 8 | 0 | 15 |
| 5 | 2 | 2 | 9 | 11 | 2 | 6 |
| Average | 2 | N/A | 5.6 | N/A | 1.2 | N/A |

[1]% Recovery calculated using only the B. subtilis CFUs.

TABLE 4

(Example 4)

| Replicate | 1 Hour | | 4 Hour | | 24 Hour | |
|---|---|---|---|---|---|---|
| | B. subtilis CFU | Other CFU | B. subtilis CFU | Other CFU | B. subtilis CFU | Other CFU |
| 1 | 0 | 0 | 0 | 2 | 0 | 0 |
| 2 | 0 | 0 | 0 | 0 | 0 | 2 |
| 3 | 0 | 0 | 1 | 1 | 0 | 1 |
| 4 | 1 | 0 | 0 | 0 | 0 | 1 |
| 5 | 0 | 0 | 0 | 0 | 0 | 3 |
| Average | 0.2 | N/A | 0.2 | N/A | 0 | N/A |
| % Recovery[1,2] | | | | | | |
| N/A | 10 | | 10 | | 0 | |

[1]Percent Recovery calculated using only the B. subtilis CFUs.
[2]Percent Recovery calculated by comparing the average CFU to those of Example 3.

This demonstrates that the compositions of the present invention provide rapid kill of bacteria and also are effective as a broad spectrum antimicrobial polymer composition as compared to comparative example, Example 3.

Each of the compositions of Examples 1, 2, and 4 were coated onto paper. The average charge decay time was determined by measuring the length of time for charge to decay to 10 percent of its value when the object is grounded. In operation, the object is charged using a dc voltage service and the drop in voltage is measured after grounding. The surface resistivity is measured by placing two electrodes on the surface and applying a fixed voltage to one electrode. The current that traveled across the surface to the other electrode is measured. Resistance then can be measured from the current and applied voltage. The results are provided in Table 5.

TABLE 5

(Antistatic Properties-Coated Free Sheet)

| | Uncoated Paper | | Example 1 | | | | Example 2 | | | |
|---|---|---|---|---|---|---|---|---|---|---|
| Polymer add-on (lbs/3000 sq ft) | — | | 5.0 | | 10.0 | | 5.0 | | 10.0 | |
| Relative Humidity (%) | 12 | 55 | 12 | 55 | 12 | 55 | 12 | 55 | 12 | 55 |
| Avg. Charge Decay Time(s) | 54.8 | 0.17 | 8.9 | 0.02 | 8.0 | 0.04 | 0.87 | 0.01 | 0.02 | 0.01 |

TABLE 5-continued (Antistatic Properties-Coated Free Sheet)

| | | | | | | | | | |
|---|---|---|---|---|---|---|---|---|---|
| Surface Resistivity (ohms/sq. @, 10V) | >E12 | 3.4E+11 | >E12 | 2.5E+11 | >E12 | 2.1+11 | 2.2E+12 | 3.8E+09 | 6.6E+10 | 1.0E+08 |

Example 4

| | | | | |
|---|---|---|---|---|
| Polymer add-on (lbs/3000 sq ft) | | 5.0 | | 10.00 |
| Relative Humidity (%) | 12 | 55 | 12 | 55 |
| Avg. Charge Decay Time(s) | 0.01 | 0.01 | 0.01 | 0.01 |
| Surface Resistivity (ohms/sq. @, 10V) | 9.0E+10 | 1.3E+08 | 1.1E+10 | 3.1E+07 |

This illustrates that antistatic properties are imparted by the composition of the present invention.

Demonstrative Examples 5-7 are intended to provide general instruction regarding the preparation of personal care substrates such as a deodorant, shampoo, and body wash. It should be understood that other personal care products could be envisioned by one skilled in the art using the polymers described in the invention.

It should be further understood that a cationic latex, such as Polymer A set forth below, can be added as an antimicrobial agent to various personal care product formulations such as those set forth in Demonstrative Examples 5-7. For example, Polymer A can provide film forming and synergistic effects when combined with the aluminum salts used as antiperspirants. It is conceivable that the formulation will have the same deodorancy effect without the use of the antiperspirant.

Polymer A

| Component Number | Batch Component | Charge Weight |
|---|---|---|
| 1 | DW | 262.50 |
| 2 | Abex ® 2525 | 4.38 |
| 3 | DW | 175.00 |
| 4 | MPEG550MA | 7.00 |
| 5 | FMQ75MC | 116.67 |
| 6 | BA | 157.50 |
| 7 | STY | 98.00 |
| 8 | DW | 3.50 |
| 9 | Wako V50 | 0.35 |
| 10 | DW | 35.00 |
| 11 | Wako V50 | 1.75 |
| 12 | DW | 3.50 |
| 13 | tBHP | 0.25 |
| 14 | DW | 3.50 |
| 15 | AWC | 0.18 |
| 16 | DW | 3.50 |
| 17 | tBHP | 0.25 |
| 18 | DW | 3.50 |
| 19 | AWC | 0.18 |
| Total | | 876.49 |

To prepare Polymer A, Components 1 and 2 were charged to a reactor. Components 3, 4, and 5 were charged to an aqueous monomer tank. Components 6 and 7 were charged to the monomer tank. The initial and feed catalyst were prepared. Approximately 10% of each monomer was charge fed to reaction. The reaction vessel was purged w/N2 and heated to approximately 155° F. While holding at temp, components 8 and 9 were charged. The reaction was held for 30 min. The feeds were initiated, with aqueous monomer over approximately 5 hours, monomer over approximately 5 hours, and cationic over approximately 5.5 hrs. (330 min.) components 12, 13, 14, and 15 were charged and the reaction was held for 15 min. Components 16, 17, 18, and 19 were charged and the reaction was held for 15 min. The reaction was allowed to cool.

Polymer A has a actual solids content of 41.10% and ~100% conversion. The particle size is 140.0 nM. The viscosity is 117.00. The final pH is 3.1.

DEMONSTRATIVE EXAMPLE 5

As one of ordinary skill in the art appreciates, deodorant compositions may comprise a variety of chemical components in various amounts. Table 6 sets forth a demonstrative deodorant/antiperspirant composition and the amounts of each component. This demonstrative deodorant/antiperspirant composition may be prepared by first combining components 1 and 3. Next, the preparer may slowly add the resulting mixture into component 2 in the presence of agitation and heat (75° C.) and then add component 4 to the resulting batch and mix the batch until component 4 dissolves. Next, the preparer slowly adds component 5 to the batch, mixes the batch until component 5 dissolves, and then cools the batch to a temperature of 45° C. The preparer then adds components 6-7 to the batch and mixes until a uniform batch results. Lastly, the preparer homogenizes the batch at 4500 rpm for 10 minutes resulting in a deodorant/antiperspirant formulation. Such deodorant compositions may be formulated as a roll-on, stick or spray.

TABLE 6

| Component No. | Component | % Weight | Batch Size |
|---|---|---|---|
| 1 | DC 245 Fluid (Dow Corning) (cyclopentasiloxane) | 49.30 | 493.00 |
| 2 | Bentone Gel ® VS-5/PC (propylene carbonate) | 13.50 | 135.00 |
| 3 | Puresyn 4 ™ (hydrogenated C6-14 olefin polymers) | 10.00 | 100.00 |
| 4 | Asensa ™ CL 110 (polyethylene) | 1.00 | 10.00 |
| 5 | Cabosil ® M5 (silica) | 0.20 | 2.00 |
| 6 | Reach ™ AZP 908 SUF (aluminum zirconium chlorhydrate) | 24.00 | 240.00 |
| 7 | Dipropylene Glycol | 2.00 | 20.00 |
| Total | | 100.00 | 1000.00 |

DEMONSTRATIVE EXAMPLE 6

Body wash formulations may comprise a variety of chemical components in various amounts. Table 7 sets forth a demonstrative body wash formulation and the amounts of each component. This demonstrative body wash formulation may be prepared by dissolving component 2 in component 1. Next, the preparer adds component 3, mixes and heats (75° C.) the resulting batch to form a first phase. The preparer then combines components 4 and 5, heats to 70° C. and mixes until the batch fully melts to form a second phase. Next, the preparer adds the second phase into the first phase with agitation and mixes until a uniform batch results. The preparer may then add components 6-8 one by one into the batch with mild agitation and cool to 40° C. Next, the preparer adds components 9 to the batch, mixes the batch and adjusts the pH to 6.0-6.5 with component 10, as needed. Finally, the preparer adjusts the viscosity to 7,000-15,000 CPS with a 20% NaCl solution, as needed. Within 30 minutes of preparation, the viscosity of the formulation of the present example was determined using a Brookfield RVT#4 at 20 RPM, 30 sec. At 12 hours post-preparation, viscosity was again determined using a Brookfield RVT#5 at 20 RPM, 30 sec.

TABLE 7

| Component No. | Component | % Weight | Batch Size |
|---|---|---|---|
| 1 | Deionized Water | 49.21 | 492.08 |
| 2 | Na₂EDTA | 0.10 | 1.00 |
| 3 | Butylene Glycol | 2.00 | 20.00 |
| 4 | Monamid ® CMA (cocamide MEA) | 2.00 | 20.00 |
| 5 | Stepan ® EGMS (glycol stearate) | 1.50 | 15.00 |
| 6 | Standapol ® A (ammonium lauryl sulfate) | 25.00 | 250.00 |
| 7 | Standapol ® ES-2 (sodium laureth sulfate) | 15.00 | 150.00 |
| 8 | Velvetex ® BK-35 (cocamidopropyl betaine) | 5.00 | 50.00 |
| 9 | Shampoo Fragrance #3599 | 0.15 | 1.50 |
| 10 | Citric Acid | 0.04 | 0.42 |
| Total | | 100.00 | 1000.00 |

DEMONSTRATIVE EXAMPLE 7

Shampoo formulations may comprise a variety of chemical components in various amounts. Table 8 sets forth a demonstrative shampoo formulation (control) and the amounts of each component. This demonstrative shampoo formulation may be prepared by first combining components 1-5 (first phase) and heating the resulting phase to a temperature of 75° C. with slow mixing. Next, the preparer may combine components 6-7 (second phase) and heat the resulting phase to a temperature of 75° C. with slow mixing. The preparer then adds the second phase to the first phase and mixes the two phases until a uniform batch at room temperature results. Next, components 8-9 may be added to the batch one at a time. Finally, the pH of the resulting batch may be adjusted to 6.0-6.5 with component 10.

TABLE 8

| Component No. | Component | % Weight | Batch Size |
|---|---|---|---|
| 1 | Water | 36.69 | 366.88 |
| 2 | Na₂EDTA | 0.05 | 0.50 |
| 3 | Bioterge AS 40 (sodium C$_{14-16}$ Olefin Sulfonate) | 45.00 | 450.00 |
| 4 | Glucamate DOE 120 (PEG-120 Methyl Glucose Dioleate) | 1.50 | 15.00 |
| 5 | Zemea ® Propanediol | 2.00 | 20.00 |
| 6 | Monamid ® CMA (cocamide MEA) | 3.00 | 30.00 |
| 7 | Velvetex ® BK-35 (cocamidopropyl betaine) | 10.00 | 100.00 |
| 8 | Kathon ® CG (methylisothiazolinone) | 0.06 | 0.60 |
| 9 | Mackpearl ® DR-140V (cocamide MEA) | 1.50 | 15.00 |
| 10 | Citric Acid | 0.20 | 2.02 |
| Total | | 100.00 | 1000.00 |

SYNTHETIC EXAMPLE 8

A deodorant composition comprising at least one antimicrobial polymer component was prepared according to the method of Demonstrative Example 5 comprising the components set forth in Table 9.

TABLE 9

| Component No. | Component | % Weight | Batch Size |
|---|---|---|---|
| 1 | DC 245 Fluid (Dow Corning) (cyclopentasiloxane) | 46.80 | 468.00 |
| 2 | Bentone Gel ® VS-5/PC (propylene carbonate) | 13.50 | 135.00 |
| 3 | Puresyn 4TM (hydrogenated C6-14 olefin polymers) | 10.00 | 100.00 |
| 4 | Asensa TM CL 110 (polyethylene) | 1.00 | 10.00 |
| 5 | Cabosil ® M5 (silica) | 0.20 | 2.00 |
| 6 | Reach TM AZP 908 SUF (aluminum zirconium chlorhydrate) | 24.00 | 240.00 |
| 7 | Dipropylene Glycol | 2.00 | 20.00 |
| 8 | Polymer A (40% Active) | 2.50 | 2.50 |
| Total | | 100.00 | 1000.00 |

SYNTHETIC EXAMPLE 9

In the present example, a base body wash formulation was prepared according to the method of Demonstrative Example 6 comprising the components set forth in Table 10. The preservative, Glydant® (DMDM Hydantoin), was mixed with component 10 and added to the batch just before pH was measured. To determine foam height, 5 grams of product and 145 grams of water were weighed and added into a blender. The product and water was grated for 10 seconds and poured into a 1000 ml graduated cylinder. The foam level was read, followed by a 2 minutes waiting period, and then the liquid level was read. To determine foam density, 10 grams of product and 145 grams of water were weighed and added into a blender. The product and water was grated for 10 seconds and the resulting foam was poured into a 100 ml graduated cylinder. A rubber stopper was then dropped into the graduated cylinder at which time a timer was started when the stopper reached the 80 ml mark. The timer was stopped when the stopper reached the 30 ml mark. The time was then recorded. Foam drainage was determined based on the amount of liquid collected at the bottom of the graduated cylinder once the stopper reached the 30 ml mark.

TABLE 10

| Component No. | Component | % Weight | Batch Size |
|---|---|---|---|
| 1 | Deionized Water | 49.01 | 490.08 |
| 2 | Na₂EDTA | 0.10 | 1.00 |
| 3 | Butylene Glycol | 2.00 | 20.00 |
| 4 | Monamid ® CMA (cocamide MEA) | 2.00 | 20.00 |
| 5 | Stepan ® EGMS (glycol stearate) | 1.50 | 15.00 |
| 6 | Standapol ® A (ammonium lauryl sulfate) | 25.00 | 250.00 |
| 7 | Standapol ® ES-2 (sodium laureth sulfate) | 15.00 | 150.00 |
| 8 | Velvetex ® BK-35 (cocamidopropyl betaine) | 5.00 | 50.00 |
| 9 | Glydant ® (DMDM hydantoin) | 0.20 | 2.00 |
| 10 | Shampoo Fragrance #3599 | 0.15 | 1.50 |
| 11 | Citric Acid | 0.04 | 0.42 |
| Total | | 100.00 | 1000.00 |

SYNTHETIC EXAMPLE 10

In the present example, a base body wash formulation was prepared containing 0.2% polyquarternium-10, such as that sold under the tradename Polymer JR 400, without glycol stearate. The polyquarternium-10 was dispersed in water and mixed until hydrated before adding components 1-3 set forth in Table 11. The body wash was then prepared according to the method set forth in Demonstrative Example 6. The viscosity, foam height, foam drainage, and foam density were measured according to the methods set forth in Synthetic Example 9.

TABLE 11

| Component No. | Component | % Weight | Batch Size |
|---|---|---|---|
| 1 | Deionized Water | 48.63 | 486.32 |
| 2 | Na₂EDTA | 0.10 | 1.00 |
| 3 | Butylene Glycol | 2.00 | 20.00 |
| 4 | Polymer JR 400 (polyquaternium-10) | 0.20 | 2.00 |
| 5 | Monamid ® CMA (cocamide MEA) | 2.00 | 20.00 |
| 6 | Standapol ® A (ammonium lauryl sulfate) | 25.00 | 250.00 |
| 7 | Standapol ® ES-2 (sodium laureth sulfate) | 15.00 | 150.00 |
| 8 | Velvetex ® BK-35 (cocamidopropyl betaine) | 5.00 | 50.00 |
| 9 | Shampoo Fragrance #3599 | 0.15 | 1.50 |
| 10 | Citric Acid | 0.04 | 0.42 |
| 11 | NaCl (20% solution) | 1.92 | 19.18 |
| Total | | 100.00 | 1000.00 |

SYNTHETIC EXAMPLE 11

In the present example, a base body wash formulation was prepared containing 0.2% polyquarternium-10 according the method set forth in Demonstrative Example 6. Table 12 sets forth the body wash formulation of the present example and the amounts of each component. The viscosity, foam height, foam drainage and foam density were measured according to the methods set forth in Synthetic Example 9.

TABLE 12

| Component No. | Component | % Weight | Batch Size |
|---|---|---|---|
| 1 | Deionized Water | 48.98 | 489.76 |
| 2 | Na₂EDTA | 0.10 | 1.00 |
| 3 | Butylene Glycol | 2.00 | 20.00 |
| 4 | Polymer JR 400 (polyquaternium-10) | 0.20 | 2.00 |
| 5 | Monamid ® CMA (cocamide MEA) | 2.00 | 20.00 |
| 6 | Stepan ® EGMS (glycol stearate) | 1.50 | 15.00 |
| 7 | Standapol ® A (ammonium lauryl sulfate) | 25.00 | 250.00 |
| 8 | Standapol ® ES-2 (sodium laureth sulfate) | 15.00 | 150.00 |
| 9 | Velvetex ® BK-35 (cocamidopropyl betaine) | 5.00 | 50.00 |
| 10 | Shampoo Fragrance #3599 | 0.15 | 1.50 |
| 11 | Citric Acid | 0.04 | 0.42 |
| 12 | NaCl (20% solution) | 0.03 | 0.32 |
| Total | | 100.00 | 1000.00 |

SYNTHETIC EXAMPLE 12

In the present example, a body wash formulation was prepared containing a 1.0% polymeric material (without glycol stearate) according the method set forth in Demonstrative Example 6. Table 13 sets forth the body wash formulation of the present example and the amounts of each component. As described in more detail herein, the present example includes Polymer A. The viscosity, foam height, foam drainage, and foam density were measured according to the methods set forth in Synthetic Example 9.

TABLE 13

| Component No. | Component | % Weight | Batch Size |
|---|---|---|---|
| 1 | Deionized Water | 45.86 | 458.60 |
| 2 | Na₂EDTA | 0.10 | 1.00 |
| 3 | Butylene Glycol | 2.00 | 20.00 |
| 4 | Polymer A (40% Active) | 2.50 | 25.00 |
| 5 | Monamid ® CMA (cocamide MEA) | 2.00 | 20.00 |
| 6 | Standapol ® A (ammonium lauryl sulfate) | 25.00 | 250.00 |
| 7 | Standapol ® ES-2 (sodium laureth sulfate) | 15.00 | 150.00 |
| 8 | Velvetex ® BK-35 (cocamidopropyl betaine) | 5.00 | 50.00 |
| 9 | Shampoo Fragrance #3599 | 0.15 | 1.50 |
| 10 | Citric Acid | 0.04 | 0.42 |
| 11 | NaCl (20% solution) | 2.35 | 23.48 |
| Total | | 100.00 | 1000.00 |

SYNTHETIC EXAMPLE 13

In the present example, yet another base body wash formulation was prepared containing a 1.0% polymeric material according the method set forth in Demonstrative Example 6. Table 14 sets forth the body wash formulation of the present example and the amounts of each component. The viscosity, foam height, foam drainage and foam density as summarized in Table 15 were measured according to the methods set forth in Synthetic Example 9.

TABLE 14

| Component No. | Component | % Weight | Batch Size |
|---|---|---|---|
| 1 | Deionized Water | 44.88 | 448.78 |
| 2 | Na₂EDTA | 0.10 | 1.00 |
| 3 | Butylene Glycol | 2.00 | 20.00 |
| 4 | Polymer A (40% Active) | 2.50 | 25.00 |
| 5 | Monamid ® CMA (cocamide MEA) | 2.00 | 20.00 |
| 6 | Stepan ® EGMS (glycol stearate) | 1.50 | 15.00 |
| 7 | Standapol ® A (ammonium lauryl sulfate) | 25.00 | 250.00 |
| 8 | Standapol ® ES-2 (sodium laureth sulfate) | 15.00 | 150.00 |
| 9 | Velvetex ® BK-35 (cocamidopropyl betaine) | 5.00 | 50.00 |
| 10 | Shampoo Fragrance #3599 | 0.15 | 1.50 |
| 11 | Citric Acid | 0.04 | 0.42 |
| 12 | NaCl (20% solution) | 1.83 | 18.30 |
| | Total | 100.00 | 1000.00 | and then the liquid level was read. To determine foam density, 10 grams of product and 145 grams of water were weighed and added into a blender. The product and water was grated for 10 seconds and the resulting foam was poured into a 100 ml graduated cylinder. A rubber stopper was then dropped into the graduated cylinder at which time a timer was started when the stopper reached the 80 ml mark. The timer was stopped when the stopper reached the 30 ml mark. The time was then recorded. Foam drainage was determined based on the amount of liquid collected at the bottom of the graduated cylinder once the stopper reached the 30 ml mark.

TABLE 16

| Component No. | Component | % Weight | Batch Size |
|---|---|---|---|
| 1 | Water | 34.12 | 341.23 |
| 2 | Na₂EDTA | 0.05 | 0.50 |
| 3 | Bioterge AS 40 (sodium $C_{14-16}$ Olefin Sulfonate) | 45.00 | 450.00 |
| 4 | Glucamate DOE 120 (PEG-120 Methyl Glucose Dioleate) | 1.50 | 15.00 |
| 5 | Zemea ® Propanediol | 2.00 | 20.00 |
| 6 | Polymer A | 2.50 | 25.00 |
| 7 | Monamid ® CMA (cocamide MEA) | 3.00 | 30.00 |
| 8 | Velvetex ® BK-35 (cocamidopropyl betaine) | 10.00 | 100.00 |
| 9 | Kathon ® CG (methylisothiazolinone) | 0.06 | 0.60 |
| 10 | Mackpearl ® DR-140V (cocamide MEA) | 1.50 | 15.00 |
| 11 | Citric Acid | 0.27 | 2.67 |
| | Total | 100.00 | 1000.00 |

TABLE 15

| | Brookfield #5 Viscosity (CPS) at 20 RPM | pH | Foam Height | Foam Drainage | Foam Density (Rubber Stopper Test) |
|---|---|---|---|---|---|
| Control (glydant) | 9,200 | 9,200 | 6.35 | 410/80 | 3 S |
| Control + polyquaternium-10 (without Stepan ® EGMS) | 5,700 | 11,000 | 6.33 | 830/<10 | 20 S |
| Control + polyquaternium-10 (with Stepan ® EGMS) | 7,200 (Brookfield #4) | 8,900 (Brookfield #4) | 6.32 | 480/70 | 4 S |
| Control + Polymer A (without Stepan ® EGMS) | 8,500 | 11,000 | 6.04 | 730/10 | 19 S |
| Control + Polymer A (with Stepan ® EGMS) | 8,000 | 10,300 | 6.06 | 470/50 | 5 S |

SYNTHETIC EXAMPLE 14

Shampoo formulations were prepared comprising at least one polymer for evaluation. In the present example, a shampoo formulation was prepared according the method set forth in Demonstrative Example 7 and contained an antimicrobial polymer. Table 16 sets forth the shampoo formulation and the amounts of each component. Viscosity was determined using a Brookfield RVT#5 at 20 RPM. To determine foam height, 5 grams of product and 145 grams of water were weighed and added into a blender. The product and water was grated for 10 seconds and poured into a 1000 ml graduated cylinder. The foam level was read, followed by a 2 minutes waiting period,

SYNTHETIC EXAMPLE 15

In the present example, another a shampoo formulation was prepared according to Demonstrative Example 7 and contained a fragrance but no antimicrobial polymeric material. Table 17 sets forth the shampoo formulation and the amounts of each component. The pH of the resulting batch was adjusted to 6.69 with component 10. The viscosity, foam height, foam drainage and foam density were measured according to the tests outlined in Synthetic Example 14.

TABLE 17

| Component No. | Component | % Weight | Batch Size |
|---|---|---|---|
| 1 | Water | 38.06 | 390.56 |
| 2 | Na$_2$EDTA | 0.05 | 0.50 |
| 3 | Bioterge AS 40 (sodium C$_{14-16}$ Olefin Sulfonate) | 45.00 | 450.00 |
| 4 | Glucamate DOE 120 (PEG-120 Methyl Glucose Dioleate) | 1.50 | 15.00 |
| 5 | Zemea ® Propanediol | 2.00 | 20.00 |
| 6 | Monamid ® CMA (cocamide MEA) | 1.50 | 15.00 |
| 7 | Velvetex ® BK-35 (cocamidopropyl betaine) | 10.00 | 100.00 |
| 8 | Kathon ® CG (methylisothiazolinone) | 0.06 | 0.60 |
| 9 | Mackpearl ® DR-140V (cocamide MEA) | 1.50 | 15.00 |
| 10 | Citric Acid | 0.13 | 1.32 |
| 11 | Mardi Gras #5544 (fragrance) | 0.20 | 2.00 |
| | Total | 100.00 | 1000.00 |

SYNTHETIC EXAMPLE 16

In the present example, another a shampoo formulation was prepared according to the method set forth in Demonstrative Example 7 that contained a fragrance as well as an antimicrobial polymeric material. Table 18 sets forth a shampoo formulation and the amounts of each component. The pH of the resulting batch was adjusted to 6.66 with component 11. The viscosity, foam height, foam drainage and foam density were measured according to the tests outlined in Synthetic Example 14. These physical properties for Demonstrative Example 7 and Synthetic Examples 14-16 are summarized in Table 19.

TABLE 18

| Component No. | Component | % Weight | Batch Size |
|---|---|---|---|
| 1 | Water | 35.52 | 355.17 |
| 2 | Na$_2$EDTA | 0.05 | 0.50 |
| 3 | Bioterge AS 40 (sodium C$_{14-16}$ Olefin Sulfonate) | 45.00 | 450.00 |
| 4 | Glucamate DOE 120 (PEG-120 Methyl Glucose Dioleate) | 1.50 | 15.00 |
| 5 | Zemea ® Propanediol | 2.00 | 20.00 |
| 6 | Polymer A | 2.50 | 25.00 |
| 7 | Monamid ® CMA (cocamide MEA) | 1.50 | 15.00 |
| 8 | Velvetex ® BK-35 (cocamidopropyl betaine) | 10.00 | 100.00 |
| 9 | Kathon ® CG (methylisothiazolinone) | 0.06 | 0.60 |
| 10 | Mackpearl ® DR-140V (cocamide MEA) | 1.50 | 15.00 |
| 11 | Citric Acid | 0.17 | 1.73 |
| 12 | Mardi Gras #5544 (fragrance) | 0.20 | 2.00 |
| | Total | 100.00 | 1000.00 |

TABLE 19

| | Brookfield #5 Viscosity (CPS) at 20 RPM | pH | Foam Height | Foam Drainage | Foam Density (Rubber Stopper Test) |
|---|---|---|---|---|---|
| Control | 49,000 | 6.47 | 760 ml | 25 ml | 22 S |
| Control + Polymer A | 45,500 | 6.10 | 790 ml | 15 ml | 25 S |
| Control + Fragrance | 8,100 | 6.69 | 800 ml | 10 ml | 26 S |
| Control + Polymer A + Fragrance | 9,200 | 6.66 | 780 ml | 10 ml | 25 S |

In the specification, there have been disclosed typical embodiments of the invention and, although specific terms are employed, they are used in a generic and descriptive sense only and not for purposes of limitation.

The specific test results observed may vary according to and depending on the particular composition, as well as the type of formulation, and mode of testing employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

That which is claimed is:

1. A substrate having applied thereto a coating or film to provide one or more antimicrobial or antistatic properties, said coating or film formed from a cationically-charged polymer composition comprising
   a noncationic ethylenically unsaturated monomer;
   an ethylenically unsaturated monomer capable of providing a cationic charge to the polymer composition; and
   a steric stabilization component incorporated into the cationically-charged polymer composition.

2. The substrate according to claim 1, wherein the substrate is at least one non-woven and woven fabric; organic and inorganic particulate, fibers or agglomerate; foam; film; cellulosic material; metal; or plastic.

3. The substrate according to claim 1, wherein the noncationic ethylenically unsaturated monomer is at least one vinyl aromatic monomer; olefin; aliphatic conjugated diene monomer; non-aromatic unsaturated mono- or dicarboxylic ester monomer; monomer based on the half ester of an unsaturated dicarboxylic acid monomer; unsaturated mono- or dicarboxylic acid monomer and derivatives thereof; nitrogen-containing monomer; phosphorous-containing monomer; sulfur-containing monomer; and vinyl ester monomer.

4. The substrate according to claim 1, wherein the ethylenically unsaturated monomer capable of providing a cationic charge to the polymer composition comprises an amine or amide monomer.

5. The substrate according to claim 1, wherein the ethylenically unsaturated monomer capable of providing a cationic charge to the polymer composition comprises a quaternized amine monomer.

6. The substrate according to claim 1, wherein the ethylenically unsaturated monomer capable of providing a cationic charge to the polymer composition comprises a quaternary derivative capable of providing hydrophobicity to the polymer composition.

7. The substrate according to claim 1, wherein the steric stabilization component is a polymerizable surfactant.

8. The substrate according to claim 1, wherein the steric stabilization component is a monomer having alkoxylated functionality or is a protective colloid.

9. The substrate according to claim 8, wherein the monomer having alkoxylated functionality is
(a) $CH_2=C(R)COO(CH_2CHR'O)_nR''$—where $R=H$, $C_1-C_4$ alkyl; and $R'=H$, $C_1-C_4$ alkyl, and $R''=H$, $C_1-C_{12}$ alkyl, and $n=1-30$;
(b) $CH_2=C(R)COO(CH_2CH_2O)_n(CH_2CHR'O)_mR''$—where $R=H$, $C_1-C_4$ alkyl, and $R'=H$, $C_1-C_4$ alkyl, and $R''=H$, $C_1-C_{12}$ alkyl, n and m each may range from 1-15;
(c) $CH_2=C(R)COO(CH_2CHR'O)_n(CH_2CH_2O)_mR''$—where $R=H$, $C_1-C_4$ alkyl, and $R'=H$, $C_1-C_4$ alkyl and $R''=H$, $C_1-C_{12}$ alkyl, n and $m=1-15$; or
(d) mixtures of (a) and (b).

10. The substrate according to claim 1, wherein the polymer composition further includes up to about 1.0 weight percent of at least one surfactant.

11. The substrate according to claim 1, wherein the at least one surfactant is a cationic surfactant, nonionic surfactant, anionic surfactant, amphoteric surfactant, or a mixture thereof.

12. The substrate according to claim 1, wherein the polymer composition further includes an antimicrobial agent or antistatic agent.

13. The substrate according to claim 12, wherein the antimicrobial agent is a chitosan-based material.

14. The substrate according to claim 12, wherein the antimicrobial agent is a metal biocide chose from silver, zinc, or salts or oxides thereof.

15. The substrate according to claim 12, wherein the antistatic agent is at least one nitrogen compound, ester of a fatty acid, polyhydric alcohol, phosphoric acid derivative, solution of at least one electrolyte in at least one liquid with a high dielectric constant, metal salt and oxides thereof, metal, carbon black, carbon nanotube or semiconductor.

16. The substrate according to claim 12, wherein the antimicrobial agent is undecylenic acid or alcohol or a reaction product of undecylenic acid with hydroxyl or acid containing material having ethylenic unsaturation.

17. The substrate according to claim 1, wherein the coating or film formed from a cationically-charged polymer composition is a latex composition.

18. The substrate according to claim 17, wherein the noncationic ethylenically unsaturated monomer comprises styrene and butylacrylate; and wherein the ethylenically unsaturated monomer capable of providing a cationic charge is dimethylaminoethyl methacrylate methyl chloride quaternary.

19. A substrate having applied thereto a coating or film to provide one or more antimicrobial or antistatic properties, said coating or film formed from a cationically-charged polymer composition consisting essentially of
about 20 to about 99 weight percent of a noncationic ethylenically unsaturated monomer;
about 0.5 to about 98 weight percent of an ethylenically unsaturated monomer capable of providing a cationic charge to the polymer composition; and
about 0 to about 75 weight percent of a steric stabilization monomer, wherein the cationically-charged polymer composition is devoid of cationic and anionic surfactants.

20. The substrate according to claim 19, wherein the substrate is at least one non-woven and woven fabric; organic and inorganic particulate, fiber or agglomerates; foam; film, cellulosic material; concrete, masonry; glass; metal; or plastic.

21. The substrate according to claim 19, wherein the noncationic ethylenically unsaturated monomer is at least one vinyl aromatic monomer; olefin; aliphatic conjugated diene monomer; non-aromatic unsaturated mono- or dicarboxylic ester monomer; monomer based on the half ester of an unsaturated dicarboxylic acid monomer; unsaturated mono- or dicarboxylic acid monomer or derivative thereof; nitrogen-containing monomer; phosphorous-containing monomer; sulfur-containing monomer; or vinyl ester monomer.

22. The substrate according to claim 19, wherein the ethylenically unsaturated monomer capable of providing a cationic charge to the polymer composition comprises an amine or amide monomer.

23. The substrate according to claim 19, wherein the ethylenically unsaturated monomer capable of providing a cationic charge to the polymer composition comprises a quaternized amine monomer.

24. The substrate according to claim 19, wherein the ethylenically unsaturated monomer capable of providing a cationic charge to the polymer composition comprises a quaternary derivative capable of providing hydrophobicity to the polymer composition.

25. The substrate according to claim 19, wherein the steric stabilization component is a monomer having alkoxylated functionality or is a protective colloid.

26. The substrate according to claim 25, wherein the monomer having alkoxylated functionality is
(a) $CH_2=C(R)COO(CH_2CHR'O)_nR''$—where $R=H$, $C_1-C_4$ alkyl; and $R'=H$, $C_1-C_4$ alkyl, and $R''=H$, $C_1-C_{12}$ alkyl, and $n=1-30$;
(b) $CH_2=C(R)COO(CH_2CH_2O)_n(CH_2CHR'O)_mR''$—where $R=H$, $C_1-C_4$ alkyl, and $R'=H$, $C_1-C_4$ alkyl, and $R''=H$, $C_1-C_{12}$ alkyl, n and m each may range from 1-15;
(c) $CH_2=C(R)COO(CH_2CHR'O)_n(CH_2CH_2O)_mR''$—where $R=H$, $C_1-C_4$ alkyl, and $R'=H$, $C_1-C_4$ alkyl and $R''=H$, $C_1-C_{12}$ alkyl, n and $m=1-15$; or
(d) mixtures of (a) and (b).

27. The substrate according to claim 19, wherein the steric stabilization component is at least one surfactant.

28. The substrate according to claim 27, wherein the at least one surfactant is a polymerizable surfactant.

29. The substrate according to claim 19, wherein the polymer composition further includes an antimicrobial agent or antistatic agent.

30. The substrate according to claim 29, wherein the antimicrobial agent is a chitosan-based material.

31. The substrate according to claim 29, wherein the antimicrobial agent is a metal biocide chosen from silver, zinc, for salts or oxides thereof.

32. The substrate according to claim 29, wherein the antistatic agent is at least one nitrogen compound, ester of at least one fatty acid, polyhydric alcohol, phosphoric acid derivative, solution of at least one electrolyte in liquid with a high dielectric constant, metallic salt or oxides thereof, metal, carbon black, carbon nanotube or semiconductor.

33. The substrate according to claim 29, wherein the antimicrobial agent is undecylenic acid or alcohol or a reaction product of undecylenic acid with hydroxyl or acid containing material having ethylenic unsaturation.

34. The substrate according to claim 19, wherein the coating or film formed from a cationically-charged polymer composition is a latex composition.

35. The substrate according to claim 34, wherein the noncationic ethylenically unsaturated monomer comprises styrene and butylacrylate; and wherein the ethylenically unsaturated monomer capable of providing a cationic charge is dimethylaminoethyl methacrylate methyl chloride quaternary.

36. A polymeric material having antimicrobial and/or antistatic properties, said polymer material comprising a base polymer blended with a cationically-charged polymer composition comprising
a nondationic ethylenically unsaturated monomer;
an ethylenically unsaturated monomer capable of providing a cationic charge to the polymer composition; and
a steric stabilization component incorporated into the cationically-charged polymer composition.

37. The polymeric material according to claim 36, wherein said base polymer is at least one polyurethane, phenolic, polyester, polyolefin, polyamide, polycarbonate, polyether, Polyether-amide, polyetherimide, polyorganosilane, polysulfone, polyisoprene, polychloroprene, acrylic, styrene-butadiene, styrene acrylonitrile, ABS, EVA, polytetrafluoroethylene, polyether-ester, or polyepoxide.

38. The polymeric material according to claim 36, wherein the polymeric material is a solid.

39. The polymeric material according to claim 36, wherein the polymeric material is a foam.

40. The polymeric material according to claim 36, wherein the noncationic ethylenically unsaturated monomer is at least one vinyl aromatic monomer; olefin; aliphatic conjugated diene monomer; non-aromatic unsaturated mono- or dicarboxylic ester monomer; monomer based on the half ester of an unsaturated dicarboxylic acid monomer; unsaturated mono- or dicarboxylic acid monomer or derivatives thereof; nitrogen-containing monomer; phosphorous-containing monomer; sulfur-containing monomer; and vinyl ester monomer.

41. The polymeric material according to claim 36, wherein the ethylenically unsaturated monomer capable of providing a cationic charge to the polymer composition comprises an amine or amide monomer.

42. The polymeric material according to claim 36, wherein the ethylenically unsaturated monomer capable of providing a cationic charge to the polymer composition comprises a quaternized amine monomer.

43. The polymeric material according to claim 36, wherein the ethylenically unsaturated monomer capable of providing a cationic charge to the polymer composition comprises a quaternary derivative capable of providing hydrophobicity to the polymer composition.

44. The polymeric material according to claim 36, wherein the steric stabilization component is a polymerizable surfactant.

45. The polymeric material according to claim 36, wherein the steric stabilization component is a monomer having alkoxylated functionality or is a protective colloid.

46. The polymeric material according to claim 45, wherein the monomer having alkoxylated functionality is
(a) $CH_2=C(R)COO(CH_2CHR'O)_nR''$—where R=H, $C_1$-$C_4$ alkyl; and R'=H, $C_1$-$C_4$ alkyl, and R''=H, $C_1$-$C_{12}$ alkyl, and n=1-30;
(b) $CH_2=C(R)COO(CH_2CH_2O)_n(CH_2CHR'O)_mR''$— where R=H, $C_1$-$C_4$ alkyl, and R'=H, $C_1$-$C_4$ alkyl, and R''=H, $C_1$-$C_{12}$ alkyl, n and m each may range from 1-15;
(c) $CH_2=C(R)COO(CH_2CHR'O)_n(CH_2CH_2O)_mR''$— where R=H, $C_1$-$C_4$ alkyl, and R'=H, $C_1$-$C_4$ alkyl and R''=H, $C_1$-$C_{12}$ alkyl, n and m=1-15; or
(d) mixtures of (a) and (b).

47. The polymeric material according to claim 36, wherein the polymer composition further includes up to about 1.0 weight percent of a cationic surfactant, nonionic surfactant, anionic surfactant, amphoteric surfactant or a mixture thereof.

48. The polymeric material according to claim 36, wherein the polymer composition further includes an antimicrobial agent or antistatic agent.

49. The polymeric material according to claim 48, wherein the antimicrobial agent is a chitosan material.

50. The polymeric material according to claim 48, wherein the antimicrobial agent is a metal biocide chosen from silver, zinc, or salts or oxides thereof.

51. The polymeric material according to claim 48, wherein the antistatic agent is at least one nitrogen compound, ester of a fatty acid or their derivatives, polyhydric alcohol or their derivatives, phosphoric acid derivative, solution of at least one electrolyte in at least one liquid with a high dielectric constants, metallic salt or oxides thereof, metal, carbon black, carbon nanotube or semiconductor.

52. The polymeric material according to claim 48, wherein the antimicrobial agent is undecylenic acid or alcohol or a reaction product of undecylenic acid with hydroxyl or acid containing material having ethylenic unsaturation.

53. A polymer material having one or more antimicrobial or antistatic properties, said polymeric material comprising a base polymer blended with a cationically charged polymer composition consisting essentially of about
20 to about 99 weight percent of a noncationic ethylenically unsaturated monomer;
about 0.5 to about 98 weight percent of an ethylenically unsaturated monomer capable of providing a cationic charge to the polymer composition; and
about 0 to about 75 weight percent of a steric stabilization monomer, wherein the cationically-charged polymer composition is devoid of cationic and anionic surfactants.

54. The polymeric material according to claim 53, wherein the noncationic ethylenically unsaturated monomer is at least one vinyl aromatic monomer; olefin; aliphatic conjugated diene monomer; non-aromatic unsaturated mono- or dicarboxylic ester monomer; monomer based on the half ester of an unsaturated dicarboxylic acid monomer; unsaturated mono- or dicarboxylic acid monomer or derivative thereof; nitrogen-containing monomer; phosphorous-containing monomer; sulfur-containing monomer; or vinyl ester monomer.

55. The polymeric material according to claim 53, wherein the ethylenically unsaturated monomer capable of providing a cationic charge to the polymer composition comprises an amine or amide monomer.

56. The polymeric material according to claim 53, wherein the ethylenically unsaturated monomer capable of providing a cationic charge to the polymer composition comprises a quaternized amine monomer.

57. The polymeric material according to claim 53, wherein the ethylenically unsaturated monomer capable of providing a cationic charge to the polymer composition comprises a quaternary derivative capable of providing hydrophobicity to the polymer composition.

58. The polymeric material according to claim 53, wherein the steric stabilization component is a monomer having alkoxylated functionality or is a protective colloid.

59. The polymeric material according to claim 58, wherein the monomer having alkoxylated functionality is
(a) $CH_2=C(R)COO(CH_2CHR'O)_nR''$—where R=H, $C_1$-$C_4$ alkyl; and R'=H, $C_1$-$C_4$ alkyl, and R''=H, $C_1$-$C_{12}$ alkyl, and n=1-30;
(b) $CH_2=C(R)COO(CH_2CH_2O)_n(CH_2CHR'O)_mR''$— where R=H, $C_1$-$C_4$ alkyl, and R'=H, $C_1$-$C_4$ alkyl, and R''=H, $C_1$-$C_{12}$ alkyl, n and m each may range from 1-15;
(c) $CH_2=C(R)COO(CH_2CHR'O)_n(CH_2CH_2O)_mR''$— where R=H, $C_1$-$C_4$ alkyl, and R'=H, $C_1$-$C_4$ alkyl and R''=H, $C_1$-$C_{12}$ alkyl, n and m=1-15; or
(d) mixtures of (a) and (b).

60. The polymeric material according to claim 53, wherein the polymer composition further includes an antimicrobial agent or antistatic agent.

61. The polymeric material according to claim 60, wherein the antimicrobial agent is a chitosan material.

62. The polymeric material according to claim 60, wherein the antimicrobial agent is a metal biocide chosen from silver, zinc, or salts or oxides thereof.

63. The polymeric material according to claim 60, wherein the antistatic agent is at least one nitrogen compound, ester of a fatty acid or their derivatives, polyhydric alcohol or their derivatives, phosphoric acid derivative, solution of at least one electrolyte in at least one liquid with a high dielectric constant, metallic salt or oxides thereof, metal, carbon black, carbon nanotube or semiconductor.

64. The polymeric material according to claim 60, wherein the antimicrobial agent is undecylenic acid, or alcohol or a reaction product of undecylenic acid with hydroxyl or acid containing material having ethylenic unsaturation.

65. The polymeric material according to claim 60, wherein said base polymer is at least one polyurethane, phenolic, polyester, polyolefin, polyamide, polycarbonate, polyether, polyether-amide, polyetherimide, polyorganosilane, polysulfone, polyisoprene, polychloroprene, acrylic, styrene-butadiene, styrene acrylonitrile, ABS, EVA, polytetrafluoroethylene, polyether-ester, or polyepoxide.

66. The polymeric material according to claim 60, wherein the polymeric material is a solid.

67. The polymeric material according to claim 60, wherein the polymeric material is a foam.

68. A method of providing one or more antimicrobial or antistatic properties to a substrate comprising applying a cationically-charged polymer composition to the substrate, wherein the polymer composition comprises
a noncationic ethylenically unsaturated monomer;
an ethylenically unsaturated monomer capable of providing a cationic charge to the polymer composition; and
a steric stabilization component incorporated into the cationically-charged polymer composition.

69. The method according to claim 68, wherein the steric stabilization component is a polymerizable surfactant.

70. The method according to claim 68, wherein the steric stabilization component is a monomer having alkoxylated functionality or is a protective colloid.

71. A method imparting one or more antimicrobial or antistatic properties to a polymeric material, the method comprising blending a base polymer with a cationically-charged polymer composition comprising
a noncationic ethylenically unsaturated monomer;
an ethylenically unsaturated monomer capable of providing a cationic charge to the polymer composition; and
a steric stabilization component incorporated into the cationically-charged polymer composition.

72. The method according to claim 71, wherein the steric stabilization component is a polymerizable surfactant.

73. The method according to claim 71, wherein the steric stabilization component is a monomer having alkoxylated functionality or is a protective colloid.

74. A personal care product comprising
a cationically-charged polymer composition comprising a noncationic ethylenically unsaturated monomer; and
an ethylenically unsaturated monomer capable of providing a cationic charge to the polymer composition.

75. The personal care product according to claim 74, wherein the cationically-charged polymer composition further comprises a steric stabilization component incorporated into the cationically-charged polymer composition.

76. The personal care product according to claim 75, wherein the steric stabilization component is a polymerizable surfactant.

77. The personal care product according to claim 75, wherein the steric stabilization component is a monomer having alkoxylated functionality or is a protective colloid.

78. The personal care product according to claim 74, wherein the noncationic ethylenically unsaturated monomer is at least one vinyl aromatic monomer; olefin; aliphatic conjugated diene monomer; non-aromatic unsaturated mono- or dicarboxylic ester monomer; monomer based on the half ester of an unsaturated dicarboxylic acid monomer; unsaturated mono- or dicarboxylic acid monomer or derivatives thereof; nitrogen-containing monomer; phosphorous-containing monomer; sulfur-containing monomer; or vinyl ester monomer.

79. The personal care product according to claim 74, wherein the ethylenically unsaturated monomer capable of providing a cationic charge to the polymer composition comprises an amine or amide monomer.

80. The personal care product according to claim 74, wherein the ethylenically unsaturated monomer capable of providing a cationic charge to the polymer composition comprises a quaternized amine monomer.

81. The personal care product according to claim 77, wherein the monomer having alkoxylated functionality is
(a) $CH_2=C(R)COO(CH_2CHR'O)_nR''$—where R=H, $C_1$-$C_4$ alkyl; and R'=H, $C_1$-$C_4$ alkyl, and R''=H, $C_1$-$C_{12}$ alkyl, and n=1-30;
(b) $CH_2=C(R)COO(CH_2CH_2O)_n(CH_2CHR'O)_mR''$— where R=H, $C_1$-$C_4$ alkyl, and R'=H, $C_1$-$C_4$ alkyl, and R''=H, $C_1$-$C_{12}$ alkyl, n and m each may range from 1-15;
(c) $CH_2=C(R)COO(CH_2CHR'O)_n(CH_2CH_2O)_mR''$— where R=H, $C_1$-$C_4$ alkyl, and R'=H, $C_1$-$C_4$ alkyl and R''=H, $C_1$-$C_{12}$ alkyl, n and m=1-15; or
(d) mixtures of (a) and (b).

82. The personal care product according to claim 74, wherein the polymer composition further includes up to about 1.0 weight percent of at least one surfactant.

83. The personal care product according to claim 82, wherein the at least one surfactant is a cationic surfactant, nonionic surfactant, anionic surfactant, amphoteric surfactant or a mixture thereof.

84. The personal care product according to claim 74, wherein the polymer composition further includes an antimicrobial agent or antistatic agent.

85. The personal care product according to claim 74, further comprising at least one active component chosen from natural plant-based wax, animal derived wax, natural mineral wax, synthetic mineral wax, synthetic wax, an alcohol comprising a carbon chain length of greater than one, an ester of an alcohol, metal stearate, carboxylic acid, fatty acid, oil, fatty amide, cosmeceutical or nutraceutical.

86. The personal care product according to claim 74, wherein the personal care product is a shampoo, deodorant, lotion, cream, body wash or cosmetic.

87. The personal care product according to claim 74, wherein the polymer composition is a latex composition.

88. The personal care product according to claim 74, wherein the noncationic ethylenically unsaturated monomer comprises styrene and butylacrylate; and wherein the ethylenically unsaturated monomer capable of providing a cationic charge is dimethylaminoethyl methacrylate methyl chloride quaternary.

89. The personal care product according to claim 88, further comprising a steric stabilization component.

90. A latex composition comprising
a noncationic ethylenically unsaturated monomer;
an ethylenically unsaturated monomer capable of providing a cationic charge to the polymer composition; and
a steric stabilization component incorporated into the latex composition.

91. The latex composition according to claim 90, wherein the ethylenically unsaturated monomer capable of providing a cationic charge to the polymer composition comprises an amine or amide monomer.

92. The latex composition according to claim 90, wherein the ethylenically unsaturated monomer capable of providing a cationic charge to the polymer composition comprises a quaternized amine monomer.

93. The latex composition according to claim 90, wherein the ethylenically unsaturated monomer capable of providing a cationic charge to the polymer composition comprises a quaternary derivative capable of providing hydrophobicity to the polymer composition.

94. The latex composition according to claim 90, wherein the steric stabilization component is a polymerizable surfactant.

95. The latex composition according to claim 90, wherein the steric stabilization component is a monomer having alkoxylated functionality or is a protective colloid.

96. The latex composition according to claim 95, wherein the monomer having alkoxylated functionality is
(a) $CH_2=C(R)COO(CH_2CHR'O)_nR''$—where R=H, $C_1$-$C_4$ alkyl; and R'=H, $C_1$-$C_4$ alkyl, and R''=H, $C_1$-$C_{12}$ alkyl, and n=1-30;
(b) $CH_2=C(R)COO(CH_2CH_2O)_n(CH_2CHR'O)_mR''$—where R=H, $C_1$-$C_4$ alkyl, and R'=H, $C_1$-$C_4$ alkyl, and R''=H, $C_1$-$C_{12}$ alkyl, n and m each may range from 1-15;
(c) $CH_2=C(R)COO(CH_2CHR'O)_n(CH_2CH_2O)_mR''$—where R=H, $C_1$-$C_4$ alkyl, and R'=H, $C_1$-$C_4$ alkyl and R''=H, $C_1$-$C_{12}$ alkyl, n and m=1-15; or
(d) mixtures of (a) and (b).

97. The latex composition according to claim 90, wherein the polymer composition further includes up to about 1.0 weight percent of at least one surfactant.

98. The latex composition according to claim 90, wherein the at least one surfactant is a cationic surfactant, nonionic surfactant, anionic surfactant, amphoteric surfactant, or a mixture thereof.

99. The latex composition according to claim 90, wherein the polymer composition further includes an antimicrobial agent or antistatic agent.

100. The latex composition according to claim 99, wherein the antimicrobial agent is a chitosan-based material.

101. The latex composition according to claim 99, wherein the antimicrobial agent is a metal biocide chosen from silver, zinc, or salts or oxides thereof.

102. The latex composition according to claim 99, wherein the antistatic agent is at least one nitrogen compound, ester of a fatty acid, polyhydric alcohol, phosphoric acid derivative, solution of at least one electrolyte in at least one liquid with a high dielectric constant, metal salt or oxide thereof, metal, carbon black, carbon nanotube or semiconductor.

103. The latex composition according to claim 99, wherein the antimicrobial agent is undecylenic acid or alcohol or a reaction product of undecylenic acid with hydroxyl or acid containing material having ethylenic unsaturation.

104. The latex composition according to claim 90, further comprising at least one active component chosen from natural plant-based wax, animal derived wax, natural mineral wax, synthetic mineral wax, synthetic wax, an alcohol comprising a carbon chain length of greater than one, an ester of an alcohol, metal stearate, carboxylic acid, fatty acid, oil, fatty amide, cosmeceutical or nutraceutical.

105. A disinfectant composition comprising
a cationically-charged polymer composition comprising a noncationic ethylenically unsaturated monomer; and
an ethylenically unsaturated monomer capable of providing a cationic charge to the polymer composition.

106. The disinfectant according to claim 105, further comprising a steric stabilization component incorporated into the cationically-charged polymer composition.

107. The disinfectant according to claim 105, further comprising at least one alcohol.

108. The disinfectant according to claim 105, further comprising at least one active component chosen from natural (plant-based wax, animal derived wax, natural mineral wax, synthetic mineral wax, synthetic wax, an alcohol comprising a carbon chain length of greater than one, an ester of an alcohol, metal stearate, carboxylic acid, fatty acid, oil, fatty amide, cosmeceutical or nutraceutical.

109. The disinfectant according to claim 105, wherein the pH of the disinfectant composition is less than or equal to 4.

110. The disinfectant according to claim 105, wherein the pH of the disinfectant composition As greater than or equal to 9.

111. The disinfectant according to claim 105, wherein the cationically-charged polymer composition is a latex composition.

112. The disinfectant according to claim 105, wherein the noncationic ethylenically unsaturated monomer comprises styrene and butylacrylate; and wherein the ethylenically unsaturated monomer capable of providing a cationic charge is dimethylaminoethyl methacrylate methyl chloride quaternary.

113. The disinfectant according to claim 112, further comprising a steric stabilization component.

114. The substrate according to claim 1, wherein the noncationic ethylenically unsaturated monomer is styrene, butyl acrylate, or a combination thereof, and wherein the ethylenically unsaturated monomer capable of providing a cationic charge to the polymer composition is dimethyl aminoethyl methacrylate.

115. The substrate according to claim 114, wherein the cationically-charged polymer composition is soluble in water, alcohol, or both alcohol and water.

116. The substrate according to claim 114, wherein the cationically-charged polymer composition further includes an antimicrobial agent or antistatic agent.

117. The polymeric material according to claim 36, wherein the noncationic ethylenically unsaturated monomer is styrene, butyl acrylate, or a combination thereof, and wherein the ethylenically unsaturated monomer capable of providing a cationic charge to the polymer composition is dimethyl aminoethyl methacrylate.

118. The polymeric material according to claim 117, wherein the polymeric material is soluble in water, alcohol, or both alcohol and water.

119. The polymeric material according to claim 117, wherein the polymeric material further includes an antimicrobial agent or antistatic agent.

120. The polymeric material according to claim 53, wherein the noncationic ethylenically unsaturated monomer is styrene, butyl acrylate, or a combination thereof, and wherein the ethylenically unsaturated monomer capable of providing a cationic charge to the polymer composition is dimethyl aminoethyl methacrylate.

121. The polymeric material according to claim 120, wherein the polymeric material is soluble in water, alcohol, or both alcohol and water.

122. The polymeric material according to claim 120, wherein the polymeric material further includes an antimicrobial agent or antistatic agent.

123. The method according to claim 68, wherein the noncationic ethylenically unsaturated monomer is styrene, butyl acrylate, or a combination thereof, and wherein the ethylenically unsaturated monomer capable of providing a cationic charge to the polymer composition is dimethyl aminoethyl methacrylate.

124. The method according to claim 123, wherein the cationically-charged polymer composition is soluble in water, alcohol, or both alcohol and water.

125. The method according to claim 123, wherein the cationically-charged polymer composition further includes an antimicrobial agent or antistatic agent.

126. The personal care product according to claim 74, wherein the noncationic ethylenically unsaturated monomer is styrene, butyl acrylate, or a combination thereof, and wherein the ethylenically unsaturated monomer capable of providing a cationic charge to the polymer composition is dimethyl aminoethyl methacrylate.

127. The personal care product according to claim 126, wherein the cationically-charged polymer composition is soluble in water, alcohol, or both alcohol and water.

128. The personal care product according to claim 126, wherein the cationically-charged polymer composition further includes an antimicrobial agent or antistatic agent.

129. The personal care product according to claim 126, wherein the cationically-charged polymer composition further comprises a steric stabilization component incorporated into the cationically-charged polymer composition.

130. The latex composition according to claim 90, wherein the noncationic ethylenically unsaturated monomer is styrene, butyl acrylate, or a combination thereof, and wherein the ethylenically unsaturated monomer capable of providing a cationic charge to the polymer composition is dimethyl aminoethyl methacrylate.

131. The latex composition according to claim 130, wherein the latex composition is soluble in water, alcohol, or both alcohol and water.

132. The latex composition according to claim 130, wherein the latex composition further includes an antimicrobial agent or antistatic agent.

133. The disinfectant according to claim 105, wherein the noncationic ethylenically unsaturated monomer is styrene, butyl acrylate, or a combination thereof, and wherein the ethylenically unsaturated monomer capable of providing a cationic charge to the polymer composition is dimethyl aminoethyl methacrylate.

134. The disinfectant according to claim 133, wherein the cationically-charged polymer composition is soluble in water, alcohol, or both alcohol and water.

135. The disinfectant according to claim 133, wherein the cationically-charged polymer composition further includes an antimicrobial agent or antistatic agent.

136. The disinfectant according to claim 133, wherein the cationically-charged polymer composition further comprises a steric stabilization component incorporated into the cationically-charged polymer composition.

* * * * *